US005889169A

United States Patent [19]
Beach et al.

[11] Patent Number: 5,889,169
[45] Date of Patent: Mar. 30, 1999

[54] CELL CYCLE REGULATORY PROTEIN P16 GENE

[75] Inventors: David H. Beach, Huntington Bay; Douglas J. Demetrick, E. Northport; Manuel Serrano, Mill Neck; Gregory J. Hannon, Huntington, all of N.Y.; Dawn E. Quelle, Cordova, Tenn.; Charles J. Sherr, Memphis, Tenn.

[73] Assignee: Cold Spring Harbor Laboratory, Cold Spring Harbor, N.Y.

[21] Appl. No.: 248,812

[22] Filed: May 25, 1994

Related U.S. Application Data

[63] Continuation-in-part of Ser. No. 227,371, filed as PCT/US93/09945, Oct. 18, 1993, which is a continuation-in-part of Ser. No. 154,915, Nov. 18, 1993, which is a continuation-in-part of Ser. No. 991,997, Dec. 17, 1992, abandoned, which is a continuation-in-part of Ser. No. 963,308, Oct. 16, 1992, which is a continuation-in-part of Ser. No. 888,178, May 26, 1992, abandoned, which is a continuation-in-part of Ser. No. 701,514, May 16, 1991.

[30] Foreign Application Priority Data

May 18, 1992 [WO] WIPO ............... PCT/US92/04146

[51] Int. Cl.$^6$ .................................................. C07H 21/04
[52] U.S. Cl. .................... 536/23.5; 536/23.7; 536/23.74; 530/358
[58] Field of Search ........................... 536/23.5, 23.7, 536/23.74; 530/350, 358

[56] References Cited

FOREIGN PATENT DOCUMENTS

| | | |
|---|---|---|
| WO 91/16429 | 10/1991 | WIPO . |
| WO 92/06180 | 4/1992 | WIPO . |
| WO 92/19749 | 11/1992 | WIPO . |
| WO 92/20316 | 11/1992 | WIPO . |
| WO 92/22635 | 12/1992 | WIPO . |
| WO 93/04701 | 3/1993 | WIPO . |
| WO 93/15227 | 8/1993 | WIPO . |
| WO 94/09135 | 4/1994 | WIPO . |

OTHER PUBLICATIONS

Chan, F.K.M. et al. "Identification of Human and Mouse p19, a Novel CDK4 AND CDK6 Inhibitor with Homology to p16Ink4" *Mol. Cell Biol.*, vol. 15, pp. 2682–2688.

Guan, K.-L et al. "Growth Suppression by p18, A p16INK4/MTS1– and p14INK4b/MTS2–Related CDK6 Inhibitor, Correlates with Wild Type pRb Function " *Genes & Development*, vol. 8, pp. 2939–2952.

Hannon, G.J. and Beach, D. "p15INK4B is a Potential Effector of TGF–beta–induced Cell Cycle Arrest" *Nature*, vol. 368, pp. 753–756.

Nobori, T. et al. "Deletions of the Cyclin–Dependent Kinase–4 Inhibitor Gene in Multiple Human Cancers" *Nature*, vol. 368, pp. 753–756.

Azzi, L. et al. (1994) "Purification of a 15–kDa cdk4– and cdk5–binding Protein" *Journal of Biological Chemistry*, vol. 269, No. 18, pp. 13279–13288.

Bates, S. et al. (1993) "CDK6 (PLSTIRE) and CDK4 (PSK–J3) are a distinct subset of the cyclin–dependent kinases that associate with cyclin D1" *Oncogene*, vol. 9, pp. 71–79.

Booher, R.N. et al. (1989) "The Fission Yeast cdc2/cdc13/suc1 Protein Kinase: Regulation of Catalytic Activity and Nuclear Localization" *Cell*, vol. 58, pp. 485–497.

Cannon–Albright, L.A. (1992) "Assignment of a Locus for Familial Melanoma, MLM, to Chromosome 9p13–p22" *Science*, vol. 258, pp. 1148–1152.

Cavanee, W.K. et al. (1983) "Expression of recessive alleles by chromosomal mechanisms in retinoblastoma" *Nature*, vol. 305, pp. 779–784.

Cavanee, W.K. et al. (1986) "Prediction of Familial Predisposition to Retinoblastoma" *New England Journal of Medicine*, vol. 314, No. 19, pp. 1201–1207.

Cheng, J.Q. et al. (1993) "Homozygous Deletions within 9p21–p22 Identify a Small Critical Region of Chromosomal Loss in Human Malignant Mesotheliomas" *Cancer Research*, vol. 53, pp. 4761–4763.

Coleman, A. et al. (1994) "Distinct Deletions of Chromosome 9p Associated with Melanoma versus Glioma, Lung Cancer and Leukemia" *Cancer Research*, vol. 54, pp. 344–348.

Ewen, M.E. et al. (1993) "Functional Interactions of the Retinoblastoma Protein with Mammalian D–type Cyclins" *Cell*, vol. 73, pp. 487–497.

Fang, F. and Newport, J.W. (1993) "Distinct roles of cdk2 and cdc2 in RP–A phosphorylatoin during the cell cycle" *Journal of Cell Science*, vol. 106, pp. 983–984.

Fields, S. and Song, O. (1989) "A novel genetic system to detect protein–protein interactions" *Nature*, vol. 340, No. 6230, pp. 245–246.

Friend, S.H. et al. (1987) "Deletions of a DNA sequence in retinoblastomas and mesenchymal tumors: Organization of the sequence and its encoded protein" *Proc. Natl. Acad. Sci. USA*, vol. 84, pp. 9059–9063.

Giordano, A. et al. (1989) "A 60 kd cdc2–Associated Polypeptide Complexes with the E1A Proteins in Adenovirus–Infected Cells" *Cell*, vol. 58, pp. 981–990.

(List continued on next page.)

*Primary Examiner*—Scott W. Houtteman
*Attorney, Agent, or Firm*—Foley, Hoag & Eliot; Matthew P. Vincent; Anita Varma

[57] ABSTRACT

The present invention relates to the discovery in eukaryotic cells, particularly mammalian cells, of a novel family of cell-cycle regulatory proteins ("CCR-proteins"). As described herein, these family of proteins includes a polypeptide having an apparent molecular weight of 16 kDa (hereinafter "p16$^{INK4}$" OR "p16") and which can function as an inhibitor of cell-cycle progression, and therefore ultimately of cell growth, and that similar to role of p21 and p53, the p16 protein may function coordinately with the cell cycle regulatory protein, retinoblastoma (Rb). Furthermore, the CCR-protein family includes a protein having an apparent molecular weight of 13.5 kDa (hereinafter "p13.5"). The presumptive role of p13.5, like p16, is in the regulation of the cell-cycle.

29 Claims, 10 Drawing Sheets

OTHER PUBLICATIONS

Graña, X. et al. (1994) "PITALRE, a nuclear CDC2–related protein kinase that phosphorylates the retinoblastoma protein in vitro" *Proc. Natl. Acad. Sci. USA* vol. 99, pp. 3834–3838.

Green, M.R. (1989) "When the Products of Oncogenes and Anti–Oncogenes Meet" *Cell,* vol. 56, pp. 1–3.

Hansen, M.F. and Cavenee, W.K. (1988) "Retinoblastoma and the progression of tumor genetics" *Trends in Genetics,* vol. 4, No. 5, pp. 125–128.

Inaba, T. et al. (1992) "Genomic Organization, Chromosomal Localization, and Independent Expression of Human Cyclin D Genes" *Genomics,* vol. 13, pp. 565–574.

Kamb, A. et al. (1994) "A Cell Cycle Regulator Potentially Involved in Genesis of Many Tumor Types" *Science,* vol. 264, pp. 436–440.

Kato, J–Y. et al. (1993) "Direct binding of cyclin D to the retinoblastoma gene product (pRb) and pRb phosphorylation by the cyclin D–dependent kinase CDK4" *Genes & Development,* vol. 7, pp. 331–342.

Knudson, Jr., A.G. (1971) "Mutation and Cancer: Statistical Study of Retinoblastoma" *Proc. Natl. Acad. Sci. USA,* vol. 68, No. 4, pp. 820–823.

Lew, D.J. et al. (1991) "Isolation of Three Novel Human Cyclins by Rescue of G1 Cyclin (Cln) Function in Yeast" *Cell,* vol. 66, pp. 1197–1206.

Matsuchime, H. et al. (1991) "Colony–Stimulating Factor 1 Regulates Novel Cyclins during the G1 Phase of the Cell Cycle" *Cell,* vol. 65, pp. 701–713.

Matsushime, H. et al. (1992) "Identification and Properties of an Atypical Catalytic Subunit ($p34^{PSK-J3}$/cdk4) for Mammalian D Type G1 Cyclins" *Cell,* vol. 71, pp. 323–334.

Motokura, T. et al. (1991) "A novel encoded by a bc/1–linked candidate oncogene" *Nature,* vol. 350, pp. 512–515.

Mowat, M. et al. (1985) "Rearrangements of the cellular p53 gene in erythroleukaemic cells transformed by Friends virus" *Nature,* vol. 314, pp. 633–636.

Paris, J. et al. (1984) "Study of the higher eukaryotic gene function CDK2 using fission yeast" *Journal of Cell Science,* vol. 107, pp. 615–623.

Parker, C. et al. (1994) "Metastasis–Associated mts1 Gene Expression Correlates with Increased p53 Detection in the B16 Murine Melanoma" *DNA and Cell Biology,* vol. 13, No. 4, pp. 343–351.

Pines, J. and Hunter, T. (1990) "Human cyclin A is adenovirus E1A–associated protein p60 and behaves differently from cyclin B" *Nature,* vol. 346, pp. 760–763.

Potashkin, J.A. and Beach, D.H. (1988) "Multiple phosphorylated forms of the product of the fission yeast cell division cycle gene $cdc2^+$" *Current Genetics,* vol. 14, pp. 235–240.

Serrano, M. et al. (1993) "A new regulatory motif in cell–cycle control causing specific inhibition of cyclin D/CDK4" *Nature,* vol. 366, pp. 704–707.

Sherr, C.J. (1993) "Mammalian $G_1$ Cyclins" *Cell,* vol. 73, pp. 1059–1065.

Walker, G.J. et al. (1994) "Refined localization of the melanoma (MLM) gene on chromosome 9p by analysis of allelic deletions" *Oncogene,* vol. 9, pp. 819–824.

Wang, J. et al. (1990) "Hepatitis B virus integrations in a cyclin A gene in a hepatocellular carcinoma" *Nature,* vol. 343, pp. 555–557.

Weinberg, R.A. (1988) "Finding the Anti–Oncogene" *Scientific American,* vol. 259, No. 3, pp. 44–51.

Xiong, Y. et al. (1992) "D Type Cyclins Associate with Multiple Protein Kinases and the DNA Replication and Repair Factor PCNA" *Cell,* vol. 71, pp. 505–514.

Xiong, Y. et al. (1991) "Human D–Type Cyclin" *Cell,* vol. 65, pp. 691–699.

Xiong, Y. et al. (1992) "Molecular Cloning and Chromosomal Mapping of CCND Genes Encoding Human D–Type Cyclins" *Genomics,* vol. 13, pp. 575–584.

Xiong, Y. et al. (1993) "p21 is a universal inhibitor of cyclin kinases" *Nature,* vol. 366, pp. 701–704.

Xiong, Y. et al. (1993) "Subunit rearrangement of the cyclin–dependent kinases is associated with cellular tranformation" *Genes & Development,* vol. 7, pp. 1572–1583.

Zhang, H. et al. (1993) "Proliferating Cell Nuclear Antigen and p21 Are Components of Multiple Cell Cycle Kinase Complexes" *Molecular Biology of the Cell,* vol. 4, pp. 897–906.

```
      Ex12                                          NTp16.2
CGGAGAGGGAATTCGGCACGAGGCAGCATGGAGCCTTCGGCTGACT
                                         Ex1
GGCTGGCCACGGCCGCGGCCCGGGGTCGGGTAGAGGAGGTGCGGGC
                                        Ex13
GCTGCTGGAGGCGGTGGCGCTGCCCAACGCACCGAATAGTTACGGT
   NTp16.3                                  Ex14
CGGAGGCCGATCCAGGTCATGGATGATGGGCAGCGCCCCGAGTGGC
              Ex2
GGAGCTGCTGCTGCTCCACGGCGCGGAGCCCAACTGCGCCGACCCC
          p16INT
GCCACTCTCACCCGACCCGTGCACCACGCTGCCCGGGAGGGCTTCT
        NTp16.5
GGACACGCTGGTGGTGCTGCACCGGGCCGGGGCGCGGCTGGACGTG
                   Ex3
CGCGATGCCTGGGGCCGTCTGCCCGTGGACCTGGCTGAGGAGCTGG

GCCATCGCGATGTCGCACGGTACCTGCGCGCCCGTGCGGGGGCAC
                                Ex15
CAGAGGCAGTAACCATGCCCGCATAGATGCCGCGGAAGGTCCCTCA
    Ex8                       Ex4
GACATCCCCGATTGAAAGAACCAGAGAGGCTCTGAGAAACCTCGGG
         Ex5
AAACTTAGATCATCAGTCACCGAAGGTCCTACAGGGCCACAACTGC

CCCCGCCACAACCCACCCCGCTTTCGTAGTTTTCATTTAGAAAATA

GAGCTTTTAAAAATGTCCTGCCTTTTAACGTAGATATAAGCCTTCC

CCCACTACCGTAAATGTCCATTTATATCATTTTTTATATATTCTTA

TAAAAATGTAAAAAGAAAACACCGCTTCTGCCTTTTCACTGTGTT
```

*Figure 1A*

```
                        Ex6
GGAGTTTTCTGGAGTGAGCACTCACGCCCTAAGCGCACATTCATGT

GGGCATTTCTTGCGAGCCTCGCAGCCTCCGGAAGCTGTCGACTTCA
                  Ex7
TGACAAGCATTTTGTGAACTAGGGAAGCTCAGGGGGGTTACTGGCT

TCTCTTGAGTCACACTGCTAGCAAATGGCAGAACCAAAGCTCAAAT

AAAAATAAAATTATTTTCATTCATTCACTCAAAAAAA
```

*Figure 1B*

```
p16ex1    < GGNGGNAAGNTGTGGGGGAAAGTTTGGGGATGGAANACCAANCCCTCCTTTCNTTACCAA
            .........+.........+.........+.........+.........+.........+ p16ex1    < ACNCTGGCTCTGNCGAGGCTNCNTCCGANTGGTNCCCCCGGGGGAGACCCAACCTGGGNC
p16ex1    < GACTTCAGGGNTGCNACATTCACTAAGTGCTNGGAGNTAATANCACCTCCTCCGAGCANx
p16ex13                         TCNCTTATTGNTAGGANATAATAACACCTCCACCGATAACT
            .........+.........+.........+.........+.........+.........+ p16ex1    < TCGCTCACAGCGTCCCCTTACCTNGANAGATACCNCGXGXTCCCTCCAGAGGATTTGAGG
p16ex13   < TCACTTACAACGTCCCNNTTCCTGGAAAGATACACAGCGTTCCCTCCAGAGGATTTGTGG
            .........+.........+.........+.........+.........+.........+ p16ex1    < GACAGGNTCGGAGGGGGCTCTTCCCCCANCACCGGAGGAAGAAAGAGGAGGGNCTGACTG
p16ex13   < GACAGGGTNGGAGNGGTCTCTTCCNCCACCACCGGAGGAAGAAAGAGGAGGGGCTGNCTG
            .........+.........+.........+.........+.........+.........+
                                                       -----Ex1A--(12)-->
p16ex1    < GTCACCAGAGGGTGGGACGGACCGCGTGCGCTCGGCGNCTNCGGAGAGGGGGAGAACAGA
p16ex13   < TTCACCAGAGGGTGGGACGGACCNCGTACGCTCGNCGNCTNCGGAGAGGGGGAGAGCAGT
            .........+.........+.........+.........+.........+.........+ p16ex1    < CAACGGGCGGCGGGGAGCAGCATGGATCCGGCGGCGGGGAGCAGCATGGANCCTTCGACT
p16ex13   < CANCGGNCGNCGGGGAGCAACATGGAACCGNCGGCGGGGAGCAGCATGGANCCTTCGGCT
            .........+.........+.........+.........+.........+.........+ p16NT2    <                 GACNNNCTCCGGCCGGNGTCGGGTAGAGGAGGTGCGGGCGCTGCTGGAG
p16ex1    < GACTGACTGCCTCGC
p16ex13   < GACTGGCTGNCCACGNCCACGNCCCGGGGTCGGGTAGAGGAGGTGCGGNCGCTNCTGGAG
            .........+.........+.........+.........+.........+.........+
                                    <---------Ex13----------
p16nt3    >                                                   CTCTNANCCCGGGTA
p16nt2    < GCGGGGGCGCTGCCCAACGCACCGAATAGTTACGGTCGGAGGCCGATCCAGGTXXGGGTA
p16ex13   < GCGGGGNCTCTGNCCAACNCGCTAAAAN
            .........+.........+.........+.........+.........+.........+ p16nt3    > GAGGGTCTGCAGCGGGAGCAGNGGATGGCGGGCGACTCTGGAGGACGAAGTTGGCAGGGG
p16nt2    < GAGGGTCTGCAGCGGGAGCAGGGGATGGCGGGCGACTCTGGAGGACGAAGTTTGCAGGGG
            .........+.........+.........+.........+.........+.........+
                                 <----------Ex1B------
p16nt3    > AATTGGAATCAGGTAGCGCTTCGANTCTCCGGAAAAAGGGGAGGCTTCCTGGGGAGTTNN
p16nt2    < AATTGGAATCAGGTAGCGCTTCGATTCTCCNGAAAAAGGGGAGGCTTCCTGGGGAGTTTT
```

*Figure 2A*

```
               .........+.........+.........+.........+.........+.........+
p16nt3  >  CAGAAGGGGTTTGTAATCACAGNCCTCCNCCTGGCGACGCCCTGGGGGGTTGGGAAGCCA
p16nt2  <  CAGAAGGGGTTTGTAATCACAGACCTCCTCCTGGCGACGTCCTGGGGGCTTGGGAAGCCA

.........+.........+.........+.........+.........+.........+
p16nt3  >  AGGAAGAGGAATGAGGAGNCACGCGCNTACAGNTCTCTCGAATNCTGANAAGATCTGAAG
p16nt2  <  AGGAAGAGGAATNAGGAGCCACGCGCGTACAGATCTCTCGAATGCTGAGAAGATCTNAAG

.........+.........+.........+.........+.........+.........+
p16nt3  >  GGGGGAACATATTTGTATTAGxATNNAAGTATGCTCTTTATCAGATACAAAATTCACGAA
p16nt2  <  GGGGGAACATATTTGTATTAGCNTCCAAGTNTNCTCTNTATCANATACAAANTxC

.........+.........+.........+.........+.........+.........+
p16nt3  >  CGTGTGGNATAAAAAGGGAGTCTTAAAGAAATNTAAGATGTGCTGGGACTACTTAGCCTC
p16nt3  >  CAANACACAGATNCCTGGATGGAGCT
```

*Figure 2B*

```
p16int  > AAAANNAAAAAAAATCTCCCAGGCCTAACATAATTNTCAGGAAAGAAATTTCAGTAGTTG
          .........+.........+.........+.........+.........+.........+ p16int  > NATCTCAGGGGAAATACAGGAAGTTAGCCTGGAGTAAAAGTCAGTCTGTCCCTGCCCCTT
          .........+.........+.........+.........+.........+.........+ p16int  > TGCTANATTGCCCGTGCCTCACAGTGCTCTCTGCCTGTGACGACAGCTCCNCAGAAGTTC
          .........+.........+.........+.........+.........+.........+ p16int  > GGAGGATATAATGGAATTCATTGTGTACTGAAGAATGGATAGAGAACTCAAGAAGGAAAT
          .........+.........+.........+.........+.........+.........+ p16int  > TGGAAACTGGAAGCAAATGTAGGGGTAATTAGACACCTGGGGCTTGTGTGGGGGTCTGCT
p16ex15 <                                         AANAAAAAAGAAATNGATAANATAGAGGAT
          .........+.........+.........+.........+.........+.........+

----------EX2A------->
p16int  > TGGCGGTGAGGGGGCTCTACACAAGCTTCCTTTCCGTCATGCCGNCCCCCACCCTGGCTC
p16ex15 < GAACANATTAAAATCAAAAAACANAACANAGACATAATAAAAAACGAGAATGTTCTAGAC
          .........+.........+.........+.........+.........+.........+

------EX14-------
p16int  > TGACCATTCTGTTCTCTCTGGCAGGTCATGATGATGGGCAGCGCCCGAGTGGCGGAGCTG
p16ex15 < NTAATCATAATTATAAAGGTCAAGACTCATTGATATnAAGGAAATTGAAGGGAAATCTTA
          .........+.........+.........+.........+.........+.........+

->
p16int  > CTGCTGCTCCACGGCGCGGAGCCCAACTGCTCCGACGCCG
p16ex2  >                                         CCTGCNACGACCCCGCCACTCTCACCCGACCCGTG
p16ex14 >          NCTCTCACGGTGGGGAGGCCAACTGCGCCGAACCCGCCACTCTCACCCGACCCGCG
p16ex15 < ACTAGCACAANNGNATNAAAAAANAATTCCCACGACACCGCCACTCTCAACGCATCCGTG
          .........+.........+.........+.........+.........+.........+ p16ex2  > CACGACGCTGTCCGGGAGGGTTTCCTGGACACGCTGGTGGTGCTGCACCGGGCCGGGGNG
p16ex14 > CACGACGGTGCCCGGGAGGGGTTCCTGGACACGCTGGTGGTGCTGCACCGGGCCGGGGCG
p16ex15 < CTCGACACTGCCCGGGAGGTCNTCCTGGACACGCTGGTGGTNCTCCACCGGNCCGGGGCA
          .........+.........+.........+.........+.........+.........+ p16ex2  > CGGTTGGACGTGCGCGATGCCTGGGGCCGCCTNCCCGTGGXACCTGGTTGAGGAGCTGGG
p16ex14 > CGGCTGGACGTTCGNGATGCCTGGGGGCNTCTNTCCGTNGXACCTGGCTGAAGAGCTGGN
p16ex15 < CGTCTGGACGTGCGCGATGCCTGGGNCCGNCTACCCGTGGTACCTGACTGAGGACCTGGG
          .........+.........+.........+.........+.........+.........+ p16ex2  > NCATCGCGATGTCGCACGGTACCTGCGCGCGGTTGCGGGGGGCACCAGAGGXNAGTNACC
p16ex14 > NCATCGNGATGTCGCACGGCCNCTGTGTGNGGNTGCGGGGGGCACCATAGGTCAGTNTCC
p16ex15 < CCATCCCGATTTCGCNGGGTANCTGNGNGNGGCTGNGGGGGCCAANAGAGGXCANTACCC
```

*Figure 2C*

```
P16EX5  <  XAAGTATGAGCGAAACNAATTGTGGTTTGAGAANAGGNAATCGTAGGGAACTTCGGGATC
           .........+.........+.........+.........+.........+.........+

P16EX5  <  CCNCNGGGANCNCCAGAACCTGAGNCGCCNATTGGAAATNACAAACTGNCTGNATCACTC
           .........+.........+.........+.........+.........+.........+

P16EX5  <  CGNACCAGGTNCAAAAGATACCTGGGGANGCGGGAAGGGAAAGACNACATCNAGACCGCC
P16EX9  <                                                             CCCC
           .........+.........+.........+.........+.........+.........+

P16EX5  <  TTCGCNCCTXGGNATTGTGAGCAGCCTCTGAGACTCATTXATATNACACTCGTXTTTCTT
P16EX9  <  ATCGCGCCTTGGGANTGTGAGCNACCATTGAGACTCATNAATATAGCACTCGTTTTTCTT
           .........+.........+.........+.........+.........+.........+

P16EX5  <  CTTACAACCCTGCGGNCCGCGCGGTCGCGCTTTCTCTGCCCTCCGCCGGGTGGACCTGGA
P16EX9  <  CTTGCAACCCTGCGGNCCGCGCGGTCGCGCTNTCTCTGCCCTCCGCNGGGTGGACCTGGA
           .........+.........+.........+.........+.........+.........+

P16EX5  <  GCGCTTGAGCGGTCGGCGCGCCTGGAGCAGCCAGGCGGNCAGTGGACTAGCTGCTGGACC
P16EX9  <  GCGCTTGAGCGGTCGGCGCNCCTGGANCAGCCAGGCGGGCAGTGGACTACCTNCTGGACC
           .........+.........+.........+.........+.........+.........+

P16EX5  <  AGGGAGGTGTGGGAGAGCGGTGGCGGCGGGTACATGCACGTGAAGCCATTGCGAGAACTT
P16EX9  <  AGGGAGGTGTGGGAGAGCGGTGNCGGCGGGTACATGCACGTGAAGCCATTGCGAGAACTT
           .........+.........+.........+.........+.........+.........+

P16EX5  <  TATCCATAAGTATTTCAATACCGGTAGGGACGGCAAGAGAGGAGGGCGGGATGTGCCACA
P16EX5  <  TATCCATAAGTATTTCAATGCCGGTAGGGACGGCAAGAGAGGAGGGCGGGATGTNCCACA
           .........+.........+.........+.........+.........+.........+

P16EX5  <  CATCTTTGACCTCAGGTTTCTAACGCCTGTTTTCTTTCTGCCCTCTGCAGACAACCCCGA
P16EX9  <  CATCTTTGACCTCAGGTTTCTAACGCCTGTTTTCTTTCTGCCCTCTGCAGACATCCCCGA
           .........+.........+.........+.........+.........+.........+

P16EX4  >                                       AGAAATTAGATCATCAGTCACCGATG
P16EX5  <  TTGAAAGAACCAGAGAGGCTCTGAGAAACC
P16EX9  <  TTGAAAGAACCAGAGAGGCTCTGAGAAACCTCCGGAAACTTAGXTCATCAXTCGCCGNAA
           .........+.........+.........+.........+.........+.........+

P16EX4  >  GTCCTACAGGGNCACAACTGNCCCCGCCACAACCCACCCCGNTTTCGTAGTTTTCATTTA
P16EX9  <  AA
```

*Figure 3A*

```
P16EX4   > GAAAATAGAGCTTTTAAAAATGTCCTGCCTTTTAACGTAGATATATGCCTTCCCCCACTA
           .........+.........+.........+.........+.........+.........+

P16EX4   > CCGNAAATGTCCATTTATATCATNTTTTATATATTCTTATAAAAATGTAAAAAAGAAAAA
           .........+.........+.........+.........+.........+.........+

P16EX4   > CACCGCTTCTGCCTTTTCACTGTGTTGGAGTTTTCTGGAGTGAGCACTCACGCCCTAAGC
           .........+.........+.........+.........+.........+.........+

P16EX6   >    CANCNATNTNCGGCATTTCTNGNGAGCCTCGTAGTCTCCGGATGNTGTCGACCTCGAG
P16EX6A  >    CANCNATNTNCGGCATTTCTNGNGAGCCTCGTAGTCTCCGGATGNTGTCGACCTCGAG
P16EX4   > GCACATTCATGTGGGCATTTCTTGCGAGCCTCGCAGNCTCCGGAAGCTGTCGACCTCGAG
           .........+.........+.........+.........+.........+.........+

P16EX6   > GGGGGGNCCNGTACCCAATTCGNCCTATNGTGAGTCGTNTTACAATTCACTGGCCGCCGT
P16EX6A  > GGGGGGNCCNGTACCCAATTCGNCCTATNGTGAGTCGTNTTACAATTCACTGGCCGCCGT
P16EX4   > GGGGGGNCCGGTACCCAATTCGCCCTATAGTGAGTCGTATTACAATTCACTGGNCGNCGN
           .........+.........+.........+.........+.........+.........+

P16EX6   > TTTXACAACGTCGXTGXACTGGGAAAACCCTGGTGTTACCCAACTTXAATCGCCTTGNAG
P16EX6A  > TTTXACAACGTCGXTGXACTGGGAAAACCCTGGTGTTACCCAACTTXAATCGCCTTGNAG
P16EX4   > TTTTACAACGTCGGTGGACTGGGAAAACCCCGGNGTTACCCAACTTTAATCGNCTTGGAG
           .........+.........+.........+.........+.........+.........+

P16EX6   > NACATCCCCCTTTXCGCCAGCTGGTGTAATAGCGANGAGGCCCGCACCGATCGCCCTTCC
P16EX6A  > NACATCCCCCTTTXCGCCAGCTGGTGTAATAGCGANGAGGCCCGCACCGATCGCCCTTCC
P16EX4   > GACATCCCCCTTTTCGCCAGNTGGGGTTATAGNGAAGAGGGCCNCACCNNTCGCCC
           .........+.........+.........+.........+.........+.........+

P16EX6   > CAACAGTTGNGCAGCCTGAATGGCGAATGGAAATTGTAAGCGTTAATATTTTGTTAAAAT
P16EX6A  > CAACAGTTGNGCAGCCTGAATGGCGAATGGAAATTGTAAGCGTTAATATTTTGTTAAAAT
           .........+.........+.........+.........+.........+.........+

P16EX6   > TCGCGTTANATCNTCGGTTAANTCAGCTCATNTTTTATCCAATAGGCCGANATCGGCANA
P16EX6A  > TCGCGTTANATCNTCGGTTAANTCAGCTCATNTTTTATCCAATAGGCCGANATCGGCANA
           .........+.........+.........+.........+.........+.........+

P16EX6   > ATCCCCAATAAATCAANAGAATAGACCGAGATAGGGTTGAGTGTCGTTCCAGTTNGGGAA
P16EX6A  > ATCCCCAATAAATCAANAGAATAGACCGAGATAGGGTTGAGTGTCGTTCCAGTTNGGGAA
           .........+.........+.........+.........+.........+.........+

P16EX6   > CANGAGTCCACTATTAAAGANCGTAGNCTCNAACGTCANAGGGCGAAAAACCNTNTTTCA
P16EX6A  > CANGAGTCCACTATTAAAGANCGTAGNCTCNAACGTCANAGGGCGAAAAACCNTNTTTCA
```

*Figure 3B*

```
                 .........+.........+..........+.........+.........+.........+
P16EX6  > GNGGATTGGNCCACTACGCNTANCC
P16EX6A > GNGGATTGGNCCACTACGCNTANCCATCACCCTATTC
```

| | H9 | U18 | CCL119 | MCF-7 | HTB 125 | SaOs2 | A431 | normal #1 | normal #2 | cell |
|---|---|---|---|---|---|---|---|---|---|---|
| | absent | absent | absent | absent | absent | altered | altered | norm | norm | exon 1 |
| | absent | absent | absent | absent | absent | altered | absent | norm | norm | exon 2 |

| | WI38 | CCL120 | HeLa | HTB100 | ZRB75 | GM130 | Tera2 | HTB172 | HTB173 | cell |
|---|---|---|---|---|---|---|---|---|---|---|
| | norm | norm | norm | norm | norm | norm | norm | norm | norm | exon 1 |
| | norm | norm | norm | norm | norm | norm | norm | norm | norm | exon 2 |

CELL CYCLE REGULATORY PROTEIN P16 GENE

RELATED APPLICATIONS

This application is a continuation-in-part of U.S. Ser. No. 08/227,371, filed as PCT/US 93/09945, Oct. 18, 1993, and entitled "Cell Cycle Regulatory Protein, and Uses Related Thereto", which is a national stage entry at PCT US 93/09945, and a continuation-in-part of U.S. Ser. No. 08/154,915 filed Nov. 8, 1993 and entitled "Cyclin Complex Rearrangements and Uses Related Thereto", which is a continuation-in-part of U.S. Ser. No. 07/991,997 filed Dec. 17, 1992 and entitled "Cyclin Complex Rearrangements and Uses Related Thereto", now abandoned, which is a continuation-in-part of U.S. Ser. No. 07/963,308 filed Oct. 16, 1992 and entitled "D-Type Cyclin and Uses Related Thereto" which is a continuation-in-part of U.S. Ser. No. 07/888,178 filed May 26, 1992 and entitled "D-Type Cyclin and Uses Related Thereto", now abandoned, which corresponds to and claims priority to Patent Cooperation Treaty Application No. PCT/US92/04146, filed May 18, 1992 and entitled "D-Type Cyclin and Uses Related Thereto", which is a CIP of U.S. Ser. No. 07/701,514, filed May 16, 1991 and entitled "D-Type Cyclin and Uses Related Thereto." The teachings of U.S. Ser. No. 08/154,915, 07/991,997, 07/963, 308, 07/888,178, 07/701,514 and the PCT Applications are incorporated herein by reference.

FUNDING

Work described herein was supported by National Institutes of Health Grant and the Howard Hughes Medical Institute. The United States Government has certain rights in the invention.

BACKGROUND OF THE INVENTION

Neoplasia is characterized by deregulated cell growth and division. Inevitably, molecular pathways controlling cell growth must interact with those regulating cell division. It was not until very recently, however, that experimental evidence became available to bring such connection to light. Cyclin A was found in association with the adenovirus oncoprotein E1A in virally transformed cells (Giordona et al. *Cell* 58:981 (1989); and Pines et al. *Nature* 346:760 (1990)). In an early hepatocellular carcinoma, the human cyclin A gene was found to be the integration site of a fragment of the hepatitis B virus, which leads to activation of cyclin A transcription and a chimeric viral cyclin A protein that is not degradable in vitro (Wang et al. *Nature* 343:555 (1990)). The cell cycle gene implicated most strongly in oncogenesis thus far is the human cyclin D1. It was originally isolated through genetic complementation of yeast $G_1$ cyclin deficient strains (Xiong et al. *Cell* 65:691 (1991); and Lew et al. *Cell* 66:1197 (1991)), as cellular genes whose transcription is stimulated by CSF-1 in murine macrophages (Matsushine et al. *Cell* 65:701 (1991)) and in the putative oncogene PRAD1 rearranged in parathyroid tumors (Montokura et al. *Nature* 350:512 (1991). Two additional human D-type cyclins, cyclins D2 and D3, were subsequently identified using PCR and low-stringency hybridization techniques (Inaba et al. *Genomics* 13:565 (1992); and Xiong et al. *Genomics* 13:575 (1992)). Cyclin D1 is genetically linked to the bcl-1 oncogene, a locus activated by translocation to an immunoglobulin gene enhancer in some B-cell lymphomas and leukemias, and located at a site of gene amplification in 15–20% of human breast cancers and 25–48% of squamous cell cancers of head and neck origin.

However, the creation of a mutant oncogene is only one of the requirements needed for tumor formation; tumorigenesis appears to also require the additional inactivation of a second class of critical genes: the "anti-oncogenes" or "tumor-suppressing genes." In their natural state these genes act to suppress cell proliferation. Damage to such genes leads to a loss of this suppression, and thereby results in tumorigenesis. Thus, the deregulation of cell growth may be mediated by either the activation of oncogenes or the inactivation of tumor-suppressing genes (Weinberg, R. A., (Sept 1988) *Scientific Amer.* pp 44–51).

Oncogenes and tumor-suppressing genes have a basic distinguished feature. The oncogenes identified thus far have arisen only in somatic cells, and thus have been incapable of transmitting their effects to the germ line of the host animal. In contrast, mutations in tumor-suppressing genes can be identified in germ line cells, and are thus transmissible to an animal's progeny.

The classic example of a hereditary cancer is retinoblastomas in children. The incidence of the retinoblastomas is determined by a tumor suppressor gene, the retinoblastoma (Rb) gene (Weinberg, R. A., (Sept 1988) *Scientific Amer.* pp 44–51; Hansen et al. (1988) *Trends Genet* 4:125–128). Individuals born with a lesion in one of the Rb alleles are predisposed to early childhood development of retinoblastomas. Inactivation or mutation of the second Rb allele in one of the somatic cells of these susceptible individuals appears to be the molecular event that leads to tumor formation (Caveneee et al. (1983) *Nature* 305:799–784; Friend et al. (1987) *PNAS* 84:9059–9063).

The Rb tumor-suppressing gene has been localized onto human chromosome 13. The mutation may be readily transmitted through the germ line of afflicted individuals (Cavenee, et al. (1986) *New Engl. J. Med* 314:1201–1207). Individuals who have mutations in only one of the two naturally present alleles of this tumor-suppressing gene are predisposed to retinoblastoma. Inactivation of the second of the two alleles is, however, required for tumorigenesis (Knudson (1971) *PNAS* 68:820–823).

A second tumor-suppressing gene is the p53 gene (Green (1989) *Cell* 56:1–3; Mowat et al (1985 *Nature* 314:633–636). The protein encoded by the p53 gene is a nuclear protein that forms a stable complex with both the SV40 large T antigen and the adenovirus E1B 55 kd protein. The p53 gene product may be inactivated by binding to these proteins.

Based on cause and effect analysis of p53 mutants, the functional role of p53 as a "cell cycle checkpoint", particularly with respect to controlling progression of a cell from G1 phase into S phase, has implicated p53 as able to directly or indirectly affect cycle cyle machinery. The first firm evidence for a specific biochemical link between p53 and the cell cycle comes a finding that p53 apparently regulates expression of a second protein, p21, which inhibits cyclin-dependent kinases (CDKs) needed to drive cells through the cell cycle, e.g. from G1 into S phase. For example, it has been demonstrated that non-viral transformation, such as resulting at least in part from a mutation of deletion of of the p53 tumor suppressor, can result in loss of p21 from cyclin/CDK complexes. As described Xiong et al. (1993) *Nature* 366:701–704, induction of p21 in response to p53 represents a plausible mechanism for effecting cell cycle arrest in response to DNA damage, and loss of p53 may deregulate growth by loss of the p21 cell-cycle inhibitor.

SUMMARY OF THE INVENTION

The present invention relates to the discovery in eukaryotic cells, particularly mammalian cells, of a novel family of cell-cycle regulatory proteins ("CCR-proteins"). As described herein, this family of proteins includes a polypeptide having an apparent molecular weight of 16 kDa (hereinafter "p16$^{INK4}$" or "p16") and which can function as an inhibitor of cell-cycle progression, and therefore ultimately of cell growth, and that similar to role of p21 and p53, the p16 protein may function coordinately with the cell cycle regulatory protein, retinoblastoma (Rb). Furthermore, the CCR-protein family includes a protein having an apparent molecular weight of 13.5 kDa (hereinafter "p13.5"). The presumptive role of p13.5, like p 16, is in the regulation of the cell-cycle.

One aspect of the invention features a substantially pure preparation of a p16$^{INK4}$ protein, or a fragment thereof, which specifically binds a cyclin-dependent kinase (CDK), wherein the p16$^{INK4}$ protein has an approximate molecular weight of 16 kDa. In a preferred embodiment: the polypeptide has an amino acid sequence at least 60% homologous to the amino acid sequence of SEQ ID No. 2; the polypeptide has an amino acid sequence at least 80% homologous to the amino acid sequence of SEQ ID No. 2; the polypeptide has an amino acid sequence at least 90% homologous to the amino acid sequence of SEQ ID No. 2; the polypeptide has an amino acid sequence identical to the amino acid sequence of SEQ ID No. 2. In a preferred embodiment: the fragment comprises at least 5 contiguous amino acid residues of SEQ ID No. 2; the fragment comprises at least 20 contiguous amino acid residues of SEQ ID No. 2; the fragment comprises at least 50 contiguous amino acid residues of SEQ ID No. 2.

Another aspect of the present invention features a substantially pure preparation of a p13.5 protein, or a fragment thereof, which specifically binds a cyclin-dependent kinase (CDK), wherein the p13.5 protein has an approximate molecular weight of 13.5 kDa. In a preferred embodiment: the polypeptide has an amino acid sequence at least 60% homologous to the amino acid sequence of SEQ ID No. 4; the polypeptide has an amino acid sequence at least 80% homologous to the amino acid sequence of SEQ ID No. 4; the polypeptide has an amino acid sequence at least 90% homologous to the amino acid sequence of SEQ ID No. 4; the polypeptide has an amino acid sequence identical to the amino acid sequence of SEQ ID No. 4. In a preferred embodiment: the fragment comprises at least 5 contiguous amino acid residues of SEQ ID No. 4; the fragment comprises at least 20 contiguous amino acid residues of SEQ ID No. 4; the fragment comprises at least 50 contiguous amino acid residues of SEQ ID No. 4.

Another aspect of the present invention features a polypeptide, of the CCR-protein family, which functions in one of either role of an agonist of cell-cycle regulation or an antagonist of cell-cycle regulation. In a preferred embodiment: the subject CCR-protein specifically binds a cyclin dependent kinase (CDK), e.g. specifically binds CDK4; e.g. specifically binds CDK6; e.g. inhibits a kinase activity of CDK4; inhibits a kinase activity of CDK6; e.g. inhibits phosphorylation of an Rb protein by CDK4. In a more preferred embodiment: the CCR-protein regulates a eukaryotic cell cycle, e.g. a mammalian cell cycle, e.g., a human cell cycle; the CCR-protein inhibits proliferation/cell growth of a eukaryotic cell, e.g., a human cell; the CCR-protein inhibits progression of a eukaryotic cell from G1 phase into S phase, e.g., inhibits progression of a mammalian cell from G1 phase into S phase, e.g., inhibits progression of a human cell from G1 phase into S phase; the CCR-protein inhibits the kinase activity of a cyclin dependent kinase (CDK), e.g. a CDK active in G1 phase, e.g. CDK 4; the CCR-protein suppresses tumor growth, e.g. in a tumor cell, e.g. in a tumor cell having an unimpaired Rb protein.

Yet another aspect of the present invention concerns an immunogen comprising a p16$^{INK4}$ protein, or a fragment thereof, in an immunogenic preparation, the immunogen being capable of eliciting an immune response specific for the p16$^{INK4}$ polypeptide; e.g. a humoral response, eg. an antibody response; e.g. a cellular response.

Another aspect of the present invention concerns an immunogen comprising a p13.5 protein, or a fragment thereof, in an immunogenic preparation, the immunogen being capable of eliciting an immune response specific for the p13.5 protein; e.g. a humoral response, eg. an antibody respone; e.g. a cellular response.

A still further aspect of the present invention features an antibody preparation specifically reactive with an epitope of the p16$^{INK4}$ immunogen.

Another aspect of the present invention features an antibody preparation specifically reactive with an epitope of the p13.5 immunogen.

Another aspect of the present invention features recombinant CCR-protein, or a fragment thereof, having an amino acid sequence preferably: at least 60% homologous to SEQ ID NO. 2; at least 80% homologous to SEQ ID No. 2; at least 90% homologous to SEQ ID No. 2; at least 95% homologous to SEQ ID No. 2; at least 60% homologous to SEQ ID NO. 4; at least 80% homologous to SEQ ID No. 4; at least 90% homologous to SEQ ID No. 4; at least 95% homologous to SEQ ID No. 4. In a preferred embodiment, the recombinant CCR-protein functions in one of either role of an agonist of cell cycle regulation or an antagonist of cell cycle regulation. In a more preferred embodiment: the CCR-protein specifically binds a cyclin dependent kinase (CDK), e.g. specifically binds CDK4; e.g. specifically binds CDK6; e.g. inhibits a kinase activity of CDK4; inhibits a kinase activity of CDK6; e.g. inhibits phosphorylation of an Rb protein by CDK4. In a more preferred embodiment: the CCR-protein regulates a eukaryotic cell cycle, e.g. a mammalian cell cycle, e.g., a human cell cycle; the CCR-protein inhibits proliferation/cell growth of a eukaryotic cell, e.g., a human cell; the CCR-protein inhibits progression of a eukaryotic cell from G1 phase into S phase, e.g., inhibits progression of a mammalian cell from G1 phase into S phase, e.g., inhibits progression of a human cell from G1 phase into S phase; the CCR-protein inhibits the kinase activity of a cyclin dependent kinase (CDK), e.g. a CDK active in G1 phase, e.g. CDK 4; the CCR-protein suppresses tumor growth, e.g. in a tumor cell, e.g. in a tumor cell having an unimpaired Rb protein.

The recombinant p16 preferably comprises: at least 5 contiguous amino acid residues of SEQ ID No. 2; at least 20 contiguous amino acid residues of SEQ ID No. 2; at least 50 contiguous amino acid residues of SEQ ID No. 2.

The recombinant p13.5 preferably comprises: at least 5 contiguous amino acid residues of SEQ ID No. 4; at least 20 contiguous amino acid residues of SEQ ID No. 4; at least 50 contiguous amino acid residues of SEQ ID No. 4.

In yet other preferred embodiments, the recombinant CCR-protein is a fusion protein further comprising a second polypeptide portion having an amino acid sequence from a protein unrelated the protein of SEQ ID No. 2 or 4. Such fusion proteins can be functional in a two-hybrid assay.

Another aspect of the present invention provides a substantially pure nucleic acid having a nucleotide sequence which encodes a CCR-protein, or a fragment thereof, having an amino acid sequence at least 60% homologous to one of either SEQ ID NO. 2 or 4. In a more preferred embodiment: the nucleic acid encodes a portein having an amino acid sequence at least 80% homologous to SEQ ID No. 2, more preferably at least 90% homologous to SEQ ID No. 2, and most preferably at least 95% homologous to SEQ ID No. 2; the nucleic acid encodes a portein having an amino acid sequence at least 80% homologous to SEQ ID No. 4, more preferably at least 90% homologous to SEQ ID No. 4, and most preferably at least 95% homologous to SEQ ID No. 4. The nucleic preferably encodes a CCR-protein which specifically binds a cyclin dependent kinase (CDK); e.g. specifically binds CDK4; e.g. specifically binds CDK6; e.g. which inhibits a kinase activity of CDK4; e.g. which inhibits phosphorylation of an Rb protein by CDK4.

In yet a further preferred embodiment, the nucleic acid hybridizes under stringent conditions to a nucleic acid probe corresponding to at least 12 consecutive nucleotides of SEQ ID No. 1; more preferably to at least 20 consecutive nucleotides of SEQ ID No. 1; more preferably to at least 40 consecutive nucleotides of SEQ ID No. 1.

In a further preferred embodiment, the nucleic acid hybridizes under stringent conditions to a nucleic acid probe corresponding to at least 12 consecutive nucleotides of SEQ ID No. 3; more preferably to at least 20 consecutive nucleotides of SEQ ID No. 3; more preferably to at least 40 consecutive nucleotides of SEQ ID No. 3.

Furthermore, in certain preferred embodiments, the CCR nucleic acid will comprise a transcriptional regulatory sequence, e.g. at least one of a transcriptional promoter or transcriptional enhancer sequence, operably linked to the CCR gene sequence so as to render the recombinant CCR gene sequence suitable for use as an expression vector.

The present invention also features transgenic non-human animals, e.g. mice, which either express a heterologous CCR gene, e.g. derived from humans, or which mis-express their own CCR gene, e.g. p16 or p13.5 expression is disrupted. Such a transgenic animal can serve as an animal model for studying cellular disorders comprising mutated or misexpressed CCR allelles.

The present invention also provides a probe/primer comprising a substantially purified oligonucleotide, wherein the oligonucleotide comprises a region of nucleotide sequence which hybridizes under stringent conditions to at least 10 consecutive nucleotides of sense or antisense sequence of either SEQ ID No. 1 or 3, or naturally occurring mutants thereof. In preferred embodiments, the probe/primer further comprises a label group attached thereto and able to be detected, e.g. the label group is selected from a group consisting of radioisotopes, fluorescent compounds, enzymes, and enzyme co-factors. Such probes can be used as a part of a diagnostic test kit for identifying transformed cells, such as for measuring a level of a $p16^{INK4}$ or p13.5 nucleic acid in a sample of cells isolated from a patient; e.g. measuring the p16 mRNA level in a cell; e.g. determining whether the genomic p16 gene has been mutated or deleted; e.g. measuring the p13.5 mRNA level in a cell; e.g. determining whether the genomic p13.5 gene has been mutated or deleted.

The present invention also provides an assay for screening test compounds for an inhibitor of an interaction of a CCR-protein, e.g. p16 or p13.5, with a cyclin dependent kinase (CDK) comprising the steps of (i) combining a CDK and a CCR-protein, e.g. which is represented by SEQ ID No. 2 or 4, under conditions wherein the CDK and the CCR-protein are able to interact; (ii) contacting the combination with a test compound; and (iii) detecting the formation of the CDK/CCR-protein complex. A statisitically significant decrease in the formation of the complex in the presence of the test compound is indicative of an inhibitor of the interaction between a CDK and the CCR-protein. In preferred embodiments: the CDK is CDK4; the CDK is CDK6; the CDK and the CCR-protein are combined in an cell-free system and contacted with said test compound; i.e. the cell-free system is selected from a group consisting of a cell lysate and a reconstituted protein mixture; the CDK and the CCR-protein are simultaneously expressed in a cell, and the cell is contacted with the test compound, e.g. the CDK and the CCR-protein comprise an interaction trap assay (two hybrid assay).

The present invention also provides a method for treating an animal having unwanted cell growth characterized by a loss of wild-type CCR-protein function, comprising administering a therapeutically effective amount of an agent able to inhibit a kinase activity of a CDK, e.g. CDK4. In one embodiment, the method comprises administering a nucleic acid construct encoding the polypeptide of SEQ ID No. 2, under conditions wherein the construct is incorporated by $p16^{INK4}$ deficient cells and the polypeptide of SEQ ID No. 2 is expressed, e.g. by gene therapy techniques. In another embodiment, the method comprises administering a nucleic acid construct encoding the polypeptide of SEQ ID No. 4, under conditions wherein the construct is incorporated by p13.5 deficient cells and the polypeptide of SEQ ID No. 4 is expressed, e.g. by gene therapy techniques.

Another aspect of the present invention provides a method of determining if a subject, e.g. a human patient, is at risk for a disorder characterized by unwanted cell proliferation, comprising detecting, in a tissue of the subject, the presence or absence of a genetic lesion characterized by at least one of (i) a mutation of a gene encoding a protein represented by one of either SEQ ID No. 2 or 4, or a homolog thereof; or (ii) the mis-expression of the CCR gene, e.g. the p16 or p13.5 gene. In preferred embodiments: detecting the genetic lesion comprises ascertaining the existence of at least one of a deletion of one or more nucleotides from said gene, an addition of one or more nucleotides to said gene, an substitution of one or more nucleotides of said gene, a gross chromosomal rearrangement of said gene, a gross alteration in the level of a messanger RNA transcript of said gene, the presence of a non-wild type splicing pattern of a messenger RNA transcript of said gene, or a non-wild type level of said protein. For example, detecting the genetic lesion can comprise (i) providing a probe/primer comprising an oligonucleotide containing a region of nucleotide sequence which hybridizes to a sense or antisense sequence of SEQ ID No. 1 or 3, or naturally occurring mutants thereof, or 5' or 3' flanking sequences naturally associated with the CCR gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the CCR gene and, optionally, of the flanking nucleic acid sequences; e.g. wherein detecting the lesion comprises utilizing the probe/primer in a polymerase chain reaction (PCR); e.g. wherein detecting the lesion comprises utilizing the probe/primer in a ligation chain reaction (LCR). In alternate embodiments, the level of said protein is detected in an immunoassay.

Other features and advantages of the invention will be apparent from the following detailed description, and from the claims. The practice of the present invention will employ, unless otherwise indicated, conventional techniques of cell biology, cell culture, molecular biology, transgenic biology, microbiology, recombinant DNA, and immunology which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press:1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

DESCRIPTION OF THE DRAWINGS

FIGS 1A–1B are a schematic representation of the p16 cDNA, indicating the location of exon boundaries and PCR primers used in the present invention.

FIGS. 2A and 2B are the genomic nucleic acid sequence for exon 1 and the non-coding sequences directly flanking exon 1. The sequence is a composite sequence from several primers. FIG. 2C is the genomic sequence about exon 2.

FIGS. 3A–3D are the genomic nucleic acid sequence for exon 3 and the non-coding sequences directly flanking exon 3. The sequence is a composite sequence from several primers.

FIG. 4 illustrates the loss of p16 sequences from the genomes of several human tumor cells, as compared to normal human controls and other human tumors.

DETAILED DESCRIPTION OF THE INVENTION

Figure 5:
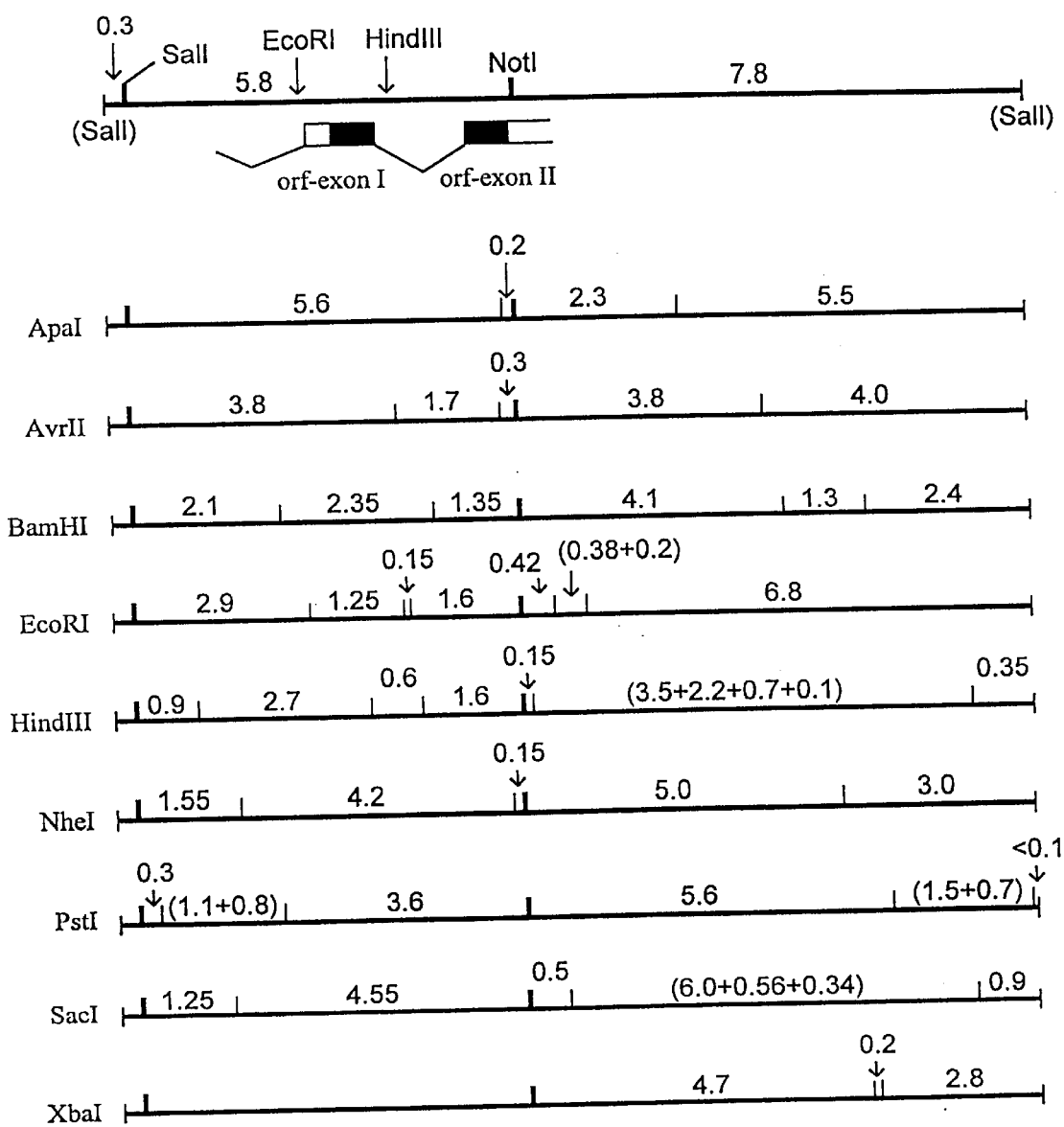
FIG. 5 illustrates the restriction map for the mouse p16 gene.

The present invention makes available diagnostic and therapeutic assays and reagents for detecting and treating transformed cells, such as may be useful in the detection of cancer. It is demonstrated below that cellular transformation is associated with selective deletion of a 16 Kd polypeptide (termed hereinafter "p16"). For example, the present invention makes available reagents, including antibodies and nucleic acid probes, for detecting altered complex formation and/or altered levels of p16 expression and/or p16 gene deletion or mutation, in order to identify transformed cells.

In addition, p16 is demonstrated below to exert an inhibitory effect on the activity of cyclin/CDK complexes, particularly those which include CDK4 or CDK6. For instance, p16 is able to inhibit the activity of cyclin D1/CDK complexes in vivo. As is generally known, cyclin D1 has been associated with a wide variety of proliferative diseases. Thus, the present invention identifies a potential inhibitor of cell proliferation resulting from oncogenic expression of cyclin D1.

Conversely, p16 can be used in assays to identify agents which decrease the ability of p16 to bind CDK4 and thereby relieve inhibition of cyclin/CDK4 complexes. In this embodiment, the reactivation of the CDK4/cyclin complexes disrupts or otherwise unbalances the cellular events occurring in a transformed cell. Such agents can be of use therapeutically to activate CDK4 complexes in cells transformed, for example, by tumor viruses. Treatment of such cells can result in enhancement of otherwise virally-suppressed cell-cycle checkpoints, such as p53, and results in the accumulation of the infected cell at the checkpoint, or alternatively, in the instance of Rb phosphorylation, cause premature progession through a checkpoint so as to result in cell death.

Furthermore, it is demonstrated that p16 is a member of a family of related cell-cycle regulatory proteins (termed "CCR-proteins"). Another member of this family, a 13.5 kDa protein (termed "p13.5"), has been cloned, and other data from hybridization and immunoprecipitation experiments indicates still further related CCR proteins exist. The presumptive role of the CCR-proteins is in the regulation of cell-cycle progression, and the members of this family are therefore likely to be involved in coordination of cell growth and/or differentiation. For instance, similar to particular characteristics of p16, certain of the other CCR-proteins bind to CDKs and are therefore likely to also be involved in modulating the activity of cyclin/CDK complexes during various stages of the cell cycle. The diversity of members of the CCR-protein family, like the diversity of CDKs, is suggestive of individualistic roles of each member of this family, which may be tissue-type of cell-type specific, occur at different points in the cell-cycle, occur as part of different extracellular or intracellular signalling pathways, or a combination thereof.

Accordingly, one aspect of this invention pertains to an isolated nucleic acid comprising the nucleotide sequence encoding a CCR-protein, fragments thereof encoding polypeptides having at least one biological activity of a CCR-protein, and/or equivalents of such nucleic acids. The term nucleic acid as used herein is intended to include such fragments and equivalents. The term equivalent is understood to include nucleotide sequences encoding functionally equivalent CCR proteins or functionally equivalent peptides having an activity of a CCR protein such as described herein. Equivalent nucleotide sequences will include sequences that differ by one or more nucleotide substitutions, additions or deletions, such as allelic variants; and will also include sequences that differ from the nucleotide sequence encoding the subject p16 protein represented by SEQ ID No. 2 or the p13.5 protein represented by SEQ ID No. 4 due to the degeneracy of the genetic code. Equivalents will also include nucleotide sequences that hybridize under stringent conditions (i.e., equivalent to about 20°–27° C. below the melting temperature ($T_m$) of the DNA duplex formed in about 1M salt) to the nucleotide sequence of the p16 protein shown in SEQ ID No. 1 or the nucleotide sequence of the p13.5 protein represented by SEQ ID No. 3. In one embodiment, equivalents will further include nucleic acid sequences derived from and evolutionarily related to the nucleotide sequence shown in either SEQ ID No. 1 or 3.

Polypeptides referred to herein as having an activity of a CCR protein are defined as peptides that have an amino acid sequence corresponding to all or a portion of the amino acid sequence of the p16 protein shown in SEQ ID No. 2 or of the p13.5 protein shown in SEQ ID No. 4, or isoforms of p16 or p13.5 (including differential splicing variants), and which have at least one biological activity of a CCR-protein. In preferred embodiments, a biological activity of a CCR-protein includes: an ability to regulate a eukaryotic cell cycle, e.g. a mammalian cell cycle, e.g., a human cell cycle; an ability to inhibit proliferation/cell growth of a eukaryotic cell, e.g. a mammalian cell, e.g., a human cell; an ability to inhibit progression of a eukaryotic cell from G1 phase into S phase, e.g., inhibit progression of a mammalian cell from G1 phase into S phase, e.g., inhibit progression of a human cell from G1 phase into S phase; an ability to inhibit the kinase activity of a cyclin dependent kinase (CDK), e.g. a CDK active in G1 phase, e.g. CDK 4, e.g. CDK6, e.g. an ability to inhibit phosphorylation of an Rb protein by CDK4. CCR-proteins of the present invention, such as the p16 protein of this family, can also have biological activities which include an ability to suppress tumor growth e.g. in a tumor having an unimpaired Rb protein. Other biological activities of the subject p16 proteins are described herein or will be reasonably apparent to those skilled in the art in light of the present disclosure. Moreover, it will be generally appreciated that, under certain circumstances, it will be advantageous to provide homologs of naturally-occurring forms of particular CCR-proteins which are either agonists or antagonists of only a subset of that proteins biological activities. Thus, specific biological effects can be elicited by treatment with a homolog of limited function, and with fewer side effects relative to treatment with agonists or antagonists which are directed to all of the biological activities of that protein. For example, p16 homologs can be generated which bind to only CDK4 without binding to CDK6 in any appreciable manner and therefore do not substantially interfere with CDK6 activity.

The term "evolutionarily related to", with respect to nucleic acid sequences encoding CCR-proteins, refers to nucleic acid sequences which have arisen naturally in an organism, including naturally occurring mutants. The term also refers to nucleic acid sequences which, while derived from a naturally occurring CCR-proteins, have been altered by mutagenesis, as for example, combinatorial mutagenesis described below, yet still encode polypeptides which have at least one activity of a CCR-protein. For instance, the sequence of p16 can be altered by mutagenesis based on amino acid substitutions derived from alignment with the p13.5 sequence.

In one embodiment, the nucleic acid is a cDNA encoding a peptide having at least one activity of a p16 protein. Preferably, the nucleic acid is a cDNA molecule comprising at least a portion of the nucleotide sequence encoding a p16 protein shown in SEQ ID No. 1. A preferred portion of the cDNA molecule shown in SEQ ID No. 1 includes the coding region of the molecule.

In another embodiment, the nucleic acid of the invention encodes a peptide having an activity of a p16 protein and comprising an amino acid sequence shown in SEQ ID No. 2. Preferred nucleic acids encode a peptide having a p16 protein activity and being at least 60% homologous, more preferably 70% homologous and most preferably 80% homologous with an amino acid sequence shown in SEQ ID No. 2. Nucleic acids which encode peptides having an activity of a p16 protein and having at least about 90%, more preferably at least about 95%, and most preferably at least about 98–99% homology with a sequence shown in SEQ ID No. 2 are also within the scope of the invention. Homology refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

In yet another embodiment, the nucleic acid is a cDNA encoding a p13.5 protein. Preferably, the nucleic acid is a cDNA molecule comprising at least a portion of the nucleotide sequence encoding a p13.5 protein shown in SEQ ID No. 3. A preferred portion of the cDNA molecule shown in SEQ ID No. 3 includes the coding region of the molecule.

In another embodiment, the nucleic acid of the invention encodes a peptide having an activity of a p13.5 protein and comprising an amino acid sequence shown in SEQ ID No. 4. Preferred nucleic acids encode a peptide having a p13.5 protein activity and being at least 60% homologous, more preferably 70% homologous and most preferably 80% homologous with an amino acid sequence shown in SEQ ID No. 4. Nucleic acids which encode peptides having an activity of a p13.5 protein, such as the ability to bind a CDK, and having at least about 90%, more preferably at least about 95%, and most preferably at least about 98–99% homology with a sequence shown in SEQ ID No. 4 are also within the scope of the invention. Homology refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

Another aspect of the invention provides a nucleic acid which hybridizes under high or low stringency conditions to a nucleic acid which encodes a peptide having all or a portion of an amino acid sequence shown in SEQ ID Nos. 2 or 12. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Isolated nucleic acids encoding peptides having a sequence which differs from the nucleotide sequence shown either SEQ ID No. 1 or 3 due to degeneracy in the genetic code are also within the scope of the invention. Such nucleic acids can encode functionally equivalent peptides (i.e., a peptide having a biological activity of a p16 protein or a p13.5 protein) but differ in sequence from the sequence shown in SEQ ID No. 1 or 3 due to degeneracy in the genetic code. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject CCR-proteins will exist among eukaryotic cells. One skilled in the art will appreciate that these variations in one or more nucleotides (up to about 3–4% of the nucleotides) of the nucleic acids encoding a particular member of the CCR-protein family may exist among individuals of a given species due to natural allelic variation. Any and all such nucleotide variations and resulting amino acid polymorphisms are within the scope of this invention.

Fragments of the nucleic acid encoding the active portion of the subject CCR-proteins are also within the scope of the invention. As used herein, a fragment of the nucleic acid encoding the active portion of a p16 protein refers to a nucleotide sequence having fewer nucleotides than the nucleotide sequence encoding the full length amino acid sequence of a p16 protein and which encodes a peptide having an activity of a p16 protein (i.e., a peptide capable of binding a CDK) as defined herein. Likewise, a fragment of the nucleic acid encoding the active portion of a p13.5 protein refers to a nucleotide sequence having fewer nucleotides than the nucleotide sequence encoding the amino acid sequence of the p13.5 protein represented by SEQ ID No. 4, and which encodes a peptide having an activity of a p16 protein (i.e., a peptide capable of binding a CDK) as defined herein. Nucleic acid fragments within the scope of the invention include those capable of hybridizing under high or low stringency conditions with nucleic acids from other species for use in screening protocols to detect homologs of the CCR-proteins of the present invention. Nucleic acids within the scope of the invention may also contain linker sequences, modified restriction endonuclease sites and other sequences useful for molecular cloning, expression or purification of such recombinant peptides.

As indicated by the examples set out below, a nucleic acid encoding a peptide having an activity of a CCR-protein may be obtained from mRNA present in any of a number of eukaryotic cells. It should also be possible to obtain nucleic acids encoding CCR-proteins from genomic DNA obtained from both adults and embryos. For example, a gene encoding a CCR-protein can be cloned from either a cDNA or a genomic library in accordance with protocols described herein, as well as those generally known to those skilled in the art. A cDNA encoding a p16 protein, for example, can be obtained by isolating total mRNA from a cell, e.g. a mammalian cell, e.g. a human cell. Double stranded cDNAs can then be prepared from the total mRNA, and subsequently inserted into a suitable plasmid or bacteriophage vector using any one of a number of known techniques. The gene encoding the p16 protein can also be cloned using established polymerase chain reaction techniques in accordance with the nucleotide sequence information provided by the invention. The nucleic acid of the invention can be DNA or RNA. A preferred nucleic acid is a CDNA encoding a p16 protein having a sequence shown in SEQ ID No. 1. Another preferred nucleic acid is a cDNA encoding a p13.5 protein having a sequence shown in SEQ ID No. 3.

This invention also provides expression vectors containing a nucleic acid encoding a peptide having an activity of a CCR-protein, operably linked to at least one regulatory sequence. Operably linked is intended to mean that the nucleotide sequence is linked to a regulatory sequence in a manner which allows expression of the nucleotide sequence. Regulatory sequences are art-recognized and are selected to direct expression of the peptide having an activity of a CCR-protein. Accordingly, the term regulatory sequence includes promoters, enhancers and other expression control elements. Such regulatory sequences are described in, for example, Goeddel; *Gene Expression Technology: Methods in Enzymology* 185, Academic Press, San Diego, Calif. (1990). It should be understood that the design of the expression vector may depend on such factors as the choice of the host cell to be transformed and/or the type of protein desired to be expressed. In one embodiment the expression vector comprises a nucleic acid sequence encoding a peptide having an activity of a p16 protein. In another embodiment, the expression vector comprises a nucleic acid sequence encoding a peptide having an activity of a p13.5 protein. Such expression vectors can be used to transfect cells in order to produce proteins or peptides, including fusion proteins or peptides encoded by nucleic acids as described herein.

Moreover, such vectors can be used as a part of a gene therapy protocol to reconstitute the function of a CCR-protein, such as p16 or p13.5, in a cell in which p16 is misexpressed. Examples of therapeutic vehicles for delivery of a CCR gene construct to a target cell are disclosed in, for example, PCT publication WO 93/04701, PCT publication WO 92/22635, PCT publication WO 92/20316, PCT publication WO 92/19749, and PCT publication WO 92/06180.

This invention also pertains to a host cell transfected to express a polypeptide having an activity of a CCR-protein. The host cell may be any prokaryotic or eukaryotic cell. For example, a p16 protein of the present invention may be expressed in bacterial cells such as *E. coli*, insect cells (baculovirus), yeast, or mammalian cells. Other suitable host cells are known to those skilled in the art.

Another aspect of the present invention concerns recombinant CCR-proteins which are encoded by genes derived from eukaryotic organisms, e.g. mammals, e.g. humans, and which have at least one biological activity of a CCR-protein, or which are naturally occurring mutants thereof. The term "recombinant protein" refers to a protein of the present invention which is produced by recombinant DNA techniques, wherein generally DNA encoding the CCR-protein is inserted into a suitable expression vector which is in turn used to transform a host cell to produce the heterologous protein. Moreover, the phrase "derived from", with respect to a recombinant gene encoding the recombinant CCR-protein, is meant to include within the meaning of "recombinant protein" those proteins having an amino acid sequence of a native CCR-protein, or an amino acid sequence similar thereto which is generated by mutations including substitutions and deletions of a naturally occurring CCR-protein of a organism. To illustrate, recombinant proteins preferred by the present invention, in addition to native p16 proteins, are those recombinantly produced proteins which are at least 60% homologous, more preferably 70% homologous and most preferably 80% homologous with an amino acid sequence shown in SEQ ID No. 2. Polypeptides having an activity of a p16 protein, such as CDK4-binding, and having at least about 90%, more preferably at least about 95%, and most preferably at least about 98–99% homology with a sequence shown in SEQ ID No. 2 are also within the scope of the invention. Similarly, in addition to native p13.5 proteins, the present invention contemplates recombinantly produced form of p13.5 homologs which are at least 60% homologous, more preferably 70% homologous and most preferably 80% homologous with an amino acid sequence shown in SEQ ID No. 4. Polypeptides having an activity of a p13.5 protein and having at least about 90%, more preferably at least about 95%, and most preferably at least about 98–99% homology with a sequence shown in SEQ ID No. 4 are likewise within the scope of the invention.

The present invention further pertains to recombinant CCR-proteins which are encoded by genes derived from a organism and which have amino acid sequences evolutionarily related to a CCR-protein represented by either SEQ ID No. 2 or 4. For instance, such evolutionarily related CCR-proteins can be xenogeneic homologs to the human p16 protein of SEQ ID No. 2 or the mouse p13.5 protein of SEQ ID No. 4. Additionally, evolutionarily related CCR-proteins encompasses other isoforms of p16 or p13.5 from the same species, e.g. which may arise from differences between allelic forms of the gene or by differential splicing of exonic sequences from a common CCR gene. The term "evolutionarily related to", with respect to amino acid sequences of the present recombinant CCR-protein, refers to CCR-proteins having amino acid sequences which have arisen naturally, as well as mutational variants of CCR-proteins which are derived, for example, by combinatorial mutagenesis. Recombinant proteins evolutionarily related to p16 protein preferred by the present invention are at least 60% homologous, more preferably 70% homologous and most preferably 80% homologous with an amino acid sequence shown in SEQ ID No. 2. Polypeptides having at least about 90%, more preferably at least about 95%, and most preferably at least about 98–99% homology with a sequence shown in SEQ ID No. 2 are also within the scope of the invention. In like manner, recombinant proteins evolutionarily related to p13.5 protein preferred by the present invention are at least 60% homologous, more preferably 70% homologous and most preferably 80% homologous with an amino acid sequence shown in SEQ ID No. 4. Polypeptides having at least about 90%, more preferably at least about 95%, and most preferably at least about 98–99% homology with a sequence shown in SEQ ID No. 4 are also within the scope of the invention.

The present invention further pertains to methods of producing the subject CCR-proteins. For example, a host cell transfected with a nucleic acid vector directing expression of a nucleotide sequence encoding the subject CCR-protein can be cultured under appropriate conditions to allow expression of the peptide to occur. The peptide may be secreted and isolated from a mixture of cells and medium containing the peptide. Alternatively, the peptide may be retained cytoplasmically and the cells harvested, lysed and the protein isolated. A cell culture includes host cells, media and other byproducts. Suitable media for cell culture are well known in the art. The peptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for particular epitopes of the subject CCR-proteins. In a preferred embodiment, the CCR-protein is a fusion protein containing a domain which facilitates its purification, such as a p16-GST fusion protein or a p13.5-GST fusion protein.

Thus, a nucleotide sequence derived from the cloning of the CCR-protein of the present invention, encoding all or a selected portion of the protein, can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. insulin, interferons, human growth hormone, IL-1, IL-2, and the like. Similar procedures, or modifications thereof, can be employed to prepare recombinant CCR-proteins, or portions thereof, by microbial means or tissue-culture technology in accord with the subject invention.

The recombinant CCR-protein can be produced by ligating the cloned gene, or a portion thereof, into a vector suitable for expression in either prokaryotic cells, eukaryotic cells, or both. Expression vehicles for production of a recombinant CCR-protein include plasmids and other vectors. For instance, suitable vectors for the expression of p16 or p13.5 include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in *Experimental Manipulation of Gene Expression*, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press:1989) Chapters 16 and 17. In some instances, it may be desirable to express the recombinant CCR-protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When expression of a portion of the CCR-protein is desired, i.e. a trunction mutant, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from E. coli (Ben-Bassat et al. (1987) J. Bacteriol. 169:751–757) and Salmonella typhimurium and its in vitro activity has been demonstrated on recombinant proteins (Miller et al. (1987) PNAS 84:2718–1722). Therefore, removal of an N-terminal methionine, if desired, can be achieved either in vivo by expressing such recombinant polypeptides in a host which produces MAP (e.g., E. coli or CM89 or S. cerevisiae), or in vitro by use of purified MAP (e.g., procedure of Miller et al.).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of a CCR-protein. For example, the VP6 capsid protein of rotavirus can be used as an immunologic carrier protein for portions of the p16 polypeptide, either in the monomeric form or in the form of a viral particle. The nucleic acid sequences corresponding to the portion of the p16 protein to which antibodies are to be raised can be incorporated into a fusion gene construct which includes coding sequences for a late vaccinia virus structural protein to produce a set of recombinant viruses expressing fusion proteins comprising a portion of the protein p16 as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a CCR-protein and the poliovirus capsid protein can be created to enhance immunogenicity of the set of polypeptide antigens (see, for example, EP Publication No. 025949; and Evans et al. (1989) *Nature* 339:385; Huang et al. (1988) *J. Virol.* 62:3855; and Schlienger et al. (1992) *J. Virol.* 66:2).

The Multiple Antigen Peptide system for peptide-based immunization can be utilized, wherein a desired portion of an CCR-protein is obtained directly from organo-chemical synthesis of the peptide onto an oligomeric branching lysine core (see, for example, Posnett et al. (1988) *JBC* 263:1719 and Nardelli et al. (1992) *J. Immunol.* 148:914). Antigenic determinants of the CCR-proteins can also be expressed and presented by bacterial cells.

In addition to utilizing fusion proteins to enhance immunogenicity, it is widely appreciated that fusion proteins can also facilitate the expression of proteins, such as the p16 protein of the present invention. For example, as described below, the p16 protein can be generated as a glutathione-S-transferase (GST- fusion protein). Such GST fusion proteins can enable easy purification of the p16 protein, such as by the use of glutathione-derivatized matrices (see, for example, *Current Protocols in Molecular Biology*, eds. Ausabel et al. (N.Y.: John Wiley & Sons, 1991)). In another embodiment, a fusion gene coding for a purification leader sequence, such as a poly-(His)/enterokinase cleavage site sequence at the N-terminus of the desired portion of the p16 protein, can allow purification of the expressed p16-fusion protein by affinity chromatography using a $Ni^{2+}$ metal resin. The purification leader sequence can then be subsequently removed by treatment with enterokinase (e.g., see Hochuli et al. 1987 *J. Chromatography* 411:177; and Janknecht et al. *PNAS* 88:8972). Correspondingly, p13.5 fusion proteins can be constructed in an analogous manner. Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

Another aspect of the invention pertains to isolated polypeptides, preferably polypeptides which can continue to possess at least one biological activity of a subject CCR-protein. In preferred embodiments, a biological activity of a CCR-protein includes: an ability to regulate a eukaryotic cell cycle, e.g. a mammalian cell cycle, e.g., a human cell cycle; an ability to inhibit proliferation/cell growth of a eukaryotic cell, e.g. a mammalian cell, e.g., a human cell; an ability to inhibit progression of a eukaryotic cell from G1 phase into S phase, e.g., inhibit progression of a mammalian cell from G1 phase into S phase, e.g., inhibit progression of a human cell from G1 phase into S phase; an ability to inhibit the kinase activity of a cyclin dependent kinase (CDK), e.g. a CDK active in G1 phase, e.g. CDK4, e.g. CDK6. Furthermore, certain CCR-proteins of the present invention, particularly p16, can have biological activities which include an ability to suppress tumor growth, e.g. in a tumor cell lacking a wild-type form of the protein or in which the endogenous CCR gene is mis-expressed. Other biological activities of the subject CCR-protein are described herein or will be reasonably apparent to those skilled in the art. In preferred embodiments of p16 agonists, a peptide having p16 biological activity may differ in amino acid sequence from the sequence shown in SEQ ID No. 2 but such differences result in a modified protein which functions in the same or similar manner as a native p16 protein or which has the same or similar characteristics of a native p16 protein, e.g. ability to bind a CDK, particularly CDK4 or CDK6. Various modifications of the p16 protein to produce these and other functionally equivalent peptides are described in detail herein. The term peptide, as used herein, refers to peptides, proteins, and polypeptides. The present invention likewise contemplates such variants of the p13.5 protein.

The present invention also makes available isolated forms of the subject CCR-proteins, which are isolated from, or otherwise substantially free of other extracellular proteins, especially cell-cycle proteins, e.g. CDKs, cyclins, p21, p19, or PCNA, normally associated with the CCR-protein. The term "substantially free of other cellular proteins" (also referred to herein as "contaminating proteins") is defined as encompassing, for example, p16 or p13.5 preparations comprising less than 20% (by dry weight) contaminating protein, and preferably comprises less than 5% contaminating protein.

Functional forms of the CCR-proteins can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins (particularly other cycle proteins such as CDK4 or CDK6, as well as other contaminating proteins). The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins) substances or solutions. The term "isolated" as also used herein with respect to nucleic acids, such as DNA or RNA, refers to molecules separated from other DNAs, or RNAs, respectively, that are present in the natural source of the macromolecule. The term isolated as used herein also refers to a nucleic acid or peptide that is substantially free of cellular material or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

Isolated peptides having the activity of one of the subject CCR-proteins can also be obtained by screening peptides recombinantly produced from the corresponding fragment of the nucleic acids encoding such peptides, e.g. fragments of the nucleic acid sequences represented by SEQ ID No. 1 or 3. In addition, fragments can be chemically synthesized using techniques known in the art such as conventional Merrifield solid phase f-Moc or t-Boc chemistry. For example, the p16 protein may be arbitrarily divided into fragments of desired length with no overlap of the fragments, or preferably divided into overlapping fragments of a desired length. The fragments can be produced (recombinantly or by chemical synthesis) and tested to identify those peptides having a p16 protein activity.

It is possible to modify the structure of a peptide having an activity of a CCR-protein for such purposes as enhancing therapeutic or prophylactic efficacy, or stability (e.g., ex vivo shelf life, and/or resistance to proteolytic degradation in vivo). Such modified peptides are considered functional equivalents of peptides having an activity of the subject CCR-proteins as defined herein. A modified peptide can be produced in which the amino acid sequence has been altered, such as by amino acid substitution, deletion, or addition.

Moreover, as described above, variant forms (e.g. mutants) of the subject CCR-proteins are also contemplated as being equivalent to those peptides and DNA molecules that are set forth in more detail, as will be appreciated by those skilled in the art. For example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur -containing= cysteine and methionine. (see, for example, *Biochemistry*, 2nd ed, Ed. by L. Stryer, WH Freeman and Co.:1981). Whether a change in the amino acid sequence of a peptide results in a functional homolog can be readily determined by assessing the ability of the variant peptide to produce a response in cells in a fashion similar to the wild-type protein. For instance, such variant forms of p16 can be assessed for their ability to complement a p16-deficient cell. Peptides in which more than one replacement has taken place can readily be tested in the same manner.

This invention further contemplates a method of generating sets of combinatorial mutants of the present CCR-proteins, as well as truncation mutants, and is especially useful for identifying potential variant sequences (e.g. homologs) that are functional in binding to a CDK, especially CDK4 or CDK6. The purpose of screening such combinatorial libraries is to generate, for example, novel p16 or p13.5 homologs which can act as either agonists or antagonist, or alternatively, possess novel activities all together. To illustrate, p16 homologs can be engineered by the present method to provide more efficient binding to CDK4, yet have a significantly reduced binding affinity for CDK6 relative to the naturally-occurring form of p16. Thus, combinatorially-derived homologs can be generated which have a selective potency relative to a naturally occurring p16. Such proteins, when expressed from recombinant DNA constructs, can be used in gene therapy protocols. Likewise, mutagenesis can give rise to CCR homologs which have intracellular half-lives dramatically different than the corresponding wild-type protein. For example, the altered protein can be rendered either more stable or less stable to proteolytic degradation or other cellular process which result in destruction of, or otherwise inactivation of, the CCR-protein. Such homologs, and the genes which encode them, can be utilized to alter the envelope of p16 or p13.5 expression by modulating the half-life of the protein. For instance, a short half-life can give rise to more transient p16 biological effects and, when part of an inducible expression system, can allow tighter control of p16 levels within the cell. As above, such proteins, and particularly their recombinant nucleic acid constructs, can be used in gene therapy protocols.

In similar fashion, CCR homologs can be generated by the present combinatorial approach to act as antagonists, in that they are able to interfere with the ability of the corresponding wild-type protein to regulate cell proliferation.

In one aspect of this method, the amino acid sequences for a population of p16 homologs or other related proteins are aligned, preferably to promote the highest homology possible. Such a population of variants can include, for example, p16 homologs from one or more species, or p16 homologs from the same species but which differ due to mutation. Amino acids which appear at each position of the aligned sequences are selected to create a degenerate set of combinatorial sequences.

In a preferred embodiment, the combinatorial CCR library is produced by way of a degenerate library of genes encoding a library of polypeptides which each include at least a portion of potential CCR-protein sequences. For instance, a mixture of synthetic oligonucleotides can be enzymatically ligated into gene sequences such that the degenerate set of potential p16 sequences or p13.5 sequences are expressible as individual polypeptides, or alternatively, as a set of larger fusion proteins (e.g. for phage display) containing the set of CCR sequences therein.

There are many ways by which the library of potential CCR homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential CCR sequences. The synthesis of degenerate oligonucleotides is well known in the art (see for example, Narang, S A (1983) *Tetrahedron* 39:3; Itakura et al. (1981) *Recombinant DNA, Proc 3rd Cleveland Sympos. Macromolecules*, ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

A wide range of techniques are known in the art for screening gene products of combinatorial libraries made by point mutations, and for screening CDNA libraries for gene products having a certain property. Such techniques will be generally adaptable for rapid screening of the gene libraries generated by the combinatorial mutagenesis of CCR homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In an illustrative embodiment of a screening assay, the candidate p16 gene products are displayed on the surface of a cell or viral particle, and the ability of particular cells or viral particles to bind a CDK, such as CDK4 or CDK6, via this gene product is detected in a "panning assay". For instance, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, fluorescently labeled molecules which bind p16, e.g. FITC-CDK4, can be used to score for potentially functional p16 homologs. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd, and fl are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) *J. Biol. Chem.* 267:16007–16010; Griffths et al. (1993) *EMBO J* 12:725–734; Clackson et al. (1991) *Nature* 352:624–628; and Barbas et al. (1992) *PNAS* 89:4457–4461).

In an illustrative embodiment, the recombinant phage antibody system (RPAS, Pharmacia Catalog number 27-9400-01) can be easily modified for use in expressing and screening CCR combinatorial libraries. For instance, the pCANTAB 5 phagemid of the RPAS kit contains the gene which encodes the phage gIII coat protein. The CCR combinatorial gene library can be cloned into the phagemid adjacent to the gIII signal sequence such that it will be expressed as a gIII fusion protein. After ligation, the phagemid is used to transform competent *E. coli* TG1 cells. Transformed cells are subsequently infected with M13KO7 helper phage to rescue the phagemid and its candidate CCR gene insert. The resulting recombinant phage contain phagemid DNA encoding a specific candidate CCR-protein and display one or more copies of the corresponding fusion coat protein. The phage-displayed candidate proteins which are capable of, for example, binding a CDK, are selected or enriched by panning. For instance, the phage library can be panned on glutathione immobilized CDK-GST fusion proteins, and unbound phage washed away from the cells. The bound phage is then isolated, and if the recombinant phage express at least one copy of the wild type gIII coat protein, they will retain their ability to infect *E. coli*. Thus, successive rounds of reinfection of *E. coli*, and panning will greatly enrich for CCR homologs, e.g. p16 or p13.5 homologs, which can then be screened for further biological activities in order to differentiate agonists and antagonists.

In light of the present discloses, other forms of mutagenesis generally applicable will be apparent to those skilled in the art in addition to the aforementioned rationale mutagenesis based on conserved versus non-conserved residues. For example, p16 or p13.5 homologs (both agonist and antagonist forms) can be generated and screened using, for example, alanine scanning mutagenesis and the like (Ruf et al. (1994) *Biochemistry* 33:1565–1572; Wang et al. (1994) *J Biol Chem* 269:3095–3099; Balint et al. (1993) *Gene* 137:109–118; Grodberg et al. (1993) *Eur J Biochem* 218:597–601; Nagashima et al. (1993) *J Biol Chem* 268:2888–2892; Lowman et al. (1991) *Biochemistry* 30:10832–10838; and Cunningham et al. (1989) *Science* 244:1081–1085), by linker scanning mutagenesis (Gustin et al. (1993) *Virology* 193:653–660; Brown et al. (1992) *Mol Cell Biol* 12:2644–2652; McKnight et al. (1982) *Science* 232:316); or by saturation mutagenesis (Meyers et al. (1986) *Science* 232:613).

Another aspect of the invention pertains to an antibody specifically reactive with one of the subject CCR-proteins. For example, by using peptides based on the cDNA sequence of the subject p16 protein, anti-p16 antisera or anti-p16 monoclonal antibodies can be made using standard methods. Likewise, anti-p13.5 antibodies can be generated. A mammal such as a mouse, a hamster or rabbit can be immunized with an immunogenic form of the peptide (e.g., an antigenic fragment which is capable of eliciting an antibody response). Techniques for conferring immunogenicity on a protein or peptide include conjugation to carriers or other techniques well known in the art. For instance, a peptidyl portion of the protein represented by either SEQ ID No. 2 or 4 can be administered in the presence of adjuvant. The progress of immunization can be monitored by detection of antibody titers in plasma or serum. Standard ELISA or other immunoassays can be used with the immunogen as antigen to assess the levels of antibodies.

Following immunization, anti-CCR antisera can be obtained and, if desired, polyclonal anti-CCR antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature,* 256: 495–497), as the human B cell hybridoma technique (Kozbar et al., (1983) *Immunology Today,* 4: 72), and the EBV-hybridoma technique to produce human monoclonal antibodies (Cole et al., (1985) *Monoclonal Antibodies and Cancer Therapy,* Alan R. Liss, Inc. pp. 77–96). Hybridoma cells can be screened immunochemically for production of antibodies specifically reactive with the CCR-protein of interest and the monoclonal antibodies isolated.

The term antibody as used herein is intended to include fragments thereof which are also specifically reactive with a CCR-protein, e.g. anti-16 or anti-p13.5 antibodies. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include banti-CCR and chimeric molecules having an anti-CCR portion.

Both monoclonal and polyclonal antibodies (Ab) directed against CCR or CCR variants, and antibody fragments such as Fab' and F(ab')$_2$, can be used to block the action of particular CCR and allow the study of the cell cycle or cell proliferation.

Antibodies which are specifically immunoreactive with one or more CCR-proteins of the present invention can also be used in immunohistochemical staining of tissue samples in order to evaluate the abundance and pattern of expression of the CCR-protein family, or particular members thereof. Anti-CCR antibodies can be used diagnostically in immuno-precipitation and immuno-blotting to detect and evaluate levels of one or more CCR-proteins in tissue or cells isolated from a bodily fluid as part of a clinical testing procedure. For instance, such measurements can be useful in predictive valuations of the onset or progression of tumors. Likewise, the ability to monitor certain CCR-protein levels in an individual can allow determination of the efficacy of a given treatment regimen for an individual afflicted with such a disorder. Diagnostic assays using anti-CCR antibodies, such as anti-p16 antibodies, can include, for example, immunoassays designed to aid in early diagnosis of a neoplastic or hyperplastic disorder, e.g. the presence of cancerous cells in the sample, e.g. to detect cells in which a lesion of a CCR gene has occurred.

For example, the present method provides a method for determining if a subject is at risk for a disorder characterized by unwanted cell proliferation. In preferred embodiments, method can be generally characterized as comprising detecting, in a tissue of said subject, the presence or absence of a genetic lesion characterized by at least one of (i) a mutation of a gene encoding a CCR-protein, such as p16 or p13.5 or (ii) the mis-expression of the CCR gene. To illustrate, such genetic lesions can be detected by ascertaining the existence of at least one of (i) a deletion of one or more nucleotides from a CCR gene, (ii) an addition of one or more nucleotides to a CCR gene, (iii) a substitution of one or more nucleotides of a CCR gene, (iv) a gross chromosomal rearrangement of a CCR gene, (v) a gross alteration in the level of a messanger RNA transcript of a CCR gene, (vi) the presence of a non-wild type splicing pattern of a messanger RNA transcript of a CCR gene, and (vii) a non-wild type level of a CCR protein. In one aspect of the invention there is provided probe/primer comprising an oligonucleotide containing a region of nucleotide sequence which is capable of hybridizing to a sense or antisense sequence of SEQ ID No. 1 or naturally occurring mutants thereof, or 5' or 3' flanking sequences or intronic sequences naturally associated with the p16 gene. In another aspect of the invention, there is provided probe/primer comprising an oligonucleotide containing a region of nucleotide sequence which is capable of hybridizing to a sense or antisense sequence of SEQ ID No. 3 or naturally occurring mutants thereof, or 5' or 3' flanking sequences or intronic sequences naturally associated with the p13.5 gene. In an illustrative embodiment, the probe is exposed to nucleic acid of a tissue sample; and the hybridization of the probe to the sample nucleic acid is detected. In certain embodiments, detection of the lesion comprises utilizing the probe/primer in a polymerase chain reaction (PCR), or, alternatively, in a ligation chain reaction (LCR), the later of which can be particularly useful for detecting even point mutations in a CCR gene. Alternatively, the level of a CCR protein can detected in an immunoassay.

Another application of anti-CCR antibodies is in the immunological screening of cDNA libraries constructed in expression vectors, such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a CCR protein, such as proteins antigenically related to p16 or p13.5, can then be detected with antibodies, as, for example, reacting nitrocellulose filters lifted from infected plates with an anti-CCR antibody. Phage, scored by this assay, can then be isolated from the infected plate. Thus, the presence of CCR homologs, such as p16 or p13.5 homologs, can be detected and cloned from other sources.

For example, the nucleotide sequence determined from the cloning of p16 from a human cell line has allowed for the generation of probes designed for use in identifying p16 homologs in other human cell types, particularly cancer or other transformed or immortalized cells, as well as p16 homologs from other animals. As described in Example 4, a p16 homolog has been cloned by moderate stringency hybridization to the human p16 coding sequence. Moreover, from sequence alignment of the human p16 and mouse p13.5 genes, degenerate primers can be designed which facilitate cloning of other members of the CCR family.

In addition, nucleotide probes can be generated from the cloned sequence of the CCR-proteins, which allow for histological screening of intact tissue and tissue samples for the presence of mRNA encoding a particular CCR-protein. Similar to the diagnostic uses of anti-CCR antibodies, the use of probes directed to CCR mRNAs, or to genomic CCR gene sequences, can be used for both predictive and therapeutic evaluation of allelic mutations which might be manifest in, for example, neoplastic or hyperplastic disorders (e.g. unwanted cell growth). Used in conjunction with anti-CCR antibody immunoassays, the nucleotide probes can help facilitate the determination of the molecular basis for a developmental disorder which may involve some abnormality associated with expression (or lack thereof) of a CCR protein. For instance, variation in p16 synthesis can be differentiated from a mutation in the p16 coding sequence.

Also, the use of anti-sense techniques (e.g. microinjection of antisense molecules, or transfection with plasmids whose transcripts are anti-sense with regard to a certain CCR mRNA) can be used to investigate role of particular CCR-proteins, e.g. p16 or p13.5, in the cell cycle and cell proliferation, in a controlled environment, by inhibiting endogenous production of the protein. Such techniques can be utilized in cell culture, but can also be used in the creation of transgenic animals.

The present invention, by making available purified and recombinant CCR-proteins, will allow the development of assays which can be used to screen for drugs which are either agonists or antagonists. By mutagenesis, and other structural surveys of the CCR-protein family, rationale drug design can be employed to manipulate a CCR-protein, or portions thereof, to generate either agonists or antagonists, as well as facilitate design of small molecule agonists and antagonists. By employing, for example, scanning mutagenesis to map the residues of p16 involved in CDK4 and/or CDK6 interaction, peptidomimetic compounds, e.g. diazepine (benzodiazepine) or isoquinoline derivatives, can be generated which are capable of binding CDK4 or CDK6 (without interfering with their ability to bind cyclins and other cell cycle proteins, yet prevent p16 from binding and inactivating CDK4. More preferable, however, are peptidomimetics which, like the p16 sequence from which they may derive, bind and inactivate a CDK, e.g. CDK4, e.g. CDK6, and can thereby provide agents which are more easily administered, e.g. systemic, and which are able to cross the cell membrane and become localized in the cell.

In another aspect, the invention features transgenic non-human animals which express a heterologous CCR gene of the present invention, or which have had one or more genomic CCR gene(s), disrupted in at least one of the tissue or cell-types of the animal. For instance, transgenic mice which have been disrupted at their p13.5 gene locus are described in Example 5.

In another aspect, the invention features an animal model for developmental diseases, which has a p16 allele which is mis-expressed. For example, a mouse can be bred which has a p16 allele deleted, or in which all or part of one or more p16 exons are deleted. Such a mouse model can then be used to study disorders arising from mis-expressed p16 genes.

I. Cyclin/CDK complexes in normal cells

As described previously (see U.S. patent applications Ser. Nos. 08/154,915, 07/991,997 and 07/963,308, as well as Xiong et al. (1993) *Nature* 366:701; Xiong et al. (1993) *Genes Dev* 7:1572; Xiong et al. (1992) *Cell* 71:505; and Zhang et al. (1993) *Mol Cell Biol* 4:897), immunological procedures have been used to establish that cyclins associate, in eukaryotic cells, with a variety of potential catalytic subunits (e.g., CDKs, such as CDK2, CDK4 and CDK5). In addition, these procedures have shown that, in untransformed cells, cyclin/CDK complexes can further associate with the replication factor PCNA and a polypeptide of 21 kDa apparent molecular weight.

To illustrate, human cyclin D1 has been associated with a wide variety of proliferative diseases. As described, in human diploid cells, specifically human diploid fibroblasts, cyclin D1 is complexed with a number of other cellular proteins. Among them are the catalytic subunits CDK2, CDK4 (previously called PSK-J3), and CDK5 (also called PSSALRE). In addition, polypeptides of 21 kDa and 36 kDa were identified in association with cyclin D1. It was shown that the 36 kDa protein is the Proliferating Cell Nuclear Antigen, PCNA. PCNA has been described as an essential accessory factor to the delta polymerase, which is required for leading-strand DNA replication and DNA repair. Cyclin D3 was also found to associate with multiple protein kinases, p21 and PCNA. It was therefore proposed that there exists a quaternary complex of D type cyclins, CDK, PCNA and p21, and that many combinatorial variations (cyclin D1, D3 with CDK2, 4 and 5) may assemble in vivo. Moreover, it was demonstrated that pSK-J3/CDK4 is the predominant cyclin dependent kinase (CDK) associated with Cyclin D1.

II. Cyclin/CDK Complexes in Transformed Cells

The importance of the quaternary complex is emphasized by the discovery that cellular transformation by DNA tumor viruses is associated with selective subunit rearrangement of the cyclin D complexes, as well as other cell-cycle complexes, including cyclin A, CDC2, CDK2, CDK4 and CDK5 complexes. In particular, introduction of SV40 DNA tumor virus or its oncogenic gene product large T antigen into normal human diploid fibroblasts (HDF) causes disruption of the association between cyclin D and PCNA, CDKs (such as CDK2, CDK4 and CDK5) and p21. For example, as described herein (and previously in U.S. patent application Ser. Nos. 08/154,915 and 07/991,997), after dissociation from cyclin D and p21, CDK4 kinase becomes associated with a 16 kDa polypeptide (p16). Similarly, SV40 transformation causes a decrease of association of p21 with cyclin A in HDF; and adenovirus-(293 cell line) or human papilloma virus- (HeLa cell line) transformed cells, p21 is completely disassociated from cyclin A. A 19 kDa peptide, p19, then appears in a complex with cyclin A. Therefore, p21 is associated with cyclin kinases only in normal, untransformed cells, whereas p16, p19 and possibly other related proteins are present in cyclin complexes in transformed cells.

Thus, striking evidence is provided that the cyclin/CDK family of enzymes that act at multiple key steps in the cell division are grossly altered in a variety of oncogenically transformed cells. For example, in transformed cells, CDK4 totally dissociates from cyclin D, PCNA, and p21 and, instead, associate exclusively with a polypeptide of 16 kd (p16). This pattern of subunit rearrangement of cyclin-CDK complexes has been discovered not only in SV40-transformed cells, but also in cells transformed with adenovirus or papilloma virus. Moreover, the pattern of subunit composition of the cyclin-CDK family was grossly abnormal in non-virally transformed cells.

In many transformed cells, cyclin and CDK's associate in binary complexes which form the core of the cell cycle regulatory machinery. In normal cells, a major fraction of the cyclin kinases acquire two additional subunits and thereby form quaternary complexes. Reconstitution of quaternary complexes in insect cells revealed that p21 is a universal inhibitor of cyclin kinases. As such, p21 inhibits cell cycle progression and cell proliferation upon overexpression in mammalian cells. Taken in conjunction with the previously demonstrated absence of p21 protein in the cell cycle kinase complexes of cells with deficient p53, these results suggest that p21 could be a transcriptional target of the tumor suppressor protein, p53. One function of p53 is to act in a cellular signaling pathway which causes cell cycle arrest following DNA damage (see for example, Kastan et al. *Cell* 71:587–5971993). It is therefore presently suggested that p21 forms a critical link between p53 and the cell cycle control machinery.

III Role of p16 in cell-cycle regulation

Deregulation of cell proliferation is a hallmark of neoplastic transformation. Alteration in growth control pathways must translate into changes in the cell cycle regulatory machinery, but the mechanism by which this occurs is largely unknown. As described above, compared to normal human fibroblasts, cells transformed with a variety of viral oncoproteins show striking changes in the subunit composition of the cyclin dependent kinases. In normal cells, CDKs exist predominantly in multiple quaternary complexes, each containing a CDK, cyclin, PCNA and p21. however, in many transformed cells PCNA and p21 are lost from these multiprotein enzymes.

Cyclin D/CDK4 kinase differs from the others in its inability to utilize histone H1 as a substrate. To date, the only substrates known for cyclin D/CDK4 kinases are the members of the RB family of "pocket" proteins (Matsushime et al., *Cell* 71:323–334 (1992)). Therefore, the effect of p21 was tested on the ability of cyclin D/CDK4 to phosphorylated RB. Insect cell lysates containing cyclin D or CDK4 alone showed little activity toward GST-RB. However, cyclin D/CDK4 binary complexes catalyzed substantial RB phosphorylation. Addition of increasing amounts of p21 resulted in the accumulation of cyclin D/CDK4/p21 ternary complexes with a corresponding inhibition of RB phosphorylation. Again, inclusion of PCNA was essentially without effect.

A. Cloning of p16, and inhibitor of CDK4

The two-hybrid screening system (Fields et al. *Nature* 340:254 (1989)) was utilized to search for proteins that could interact with human CDK4, and more specifically, to isolate a cDNA encoding p16. Two-hybrid screening relies on reconstituting a functional GAL4 activator from two separated fusion proteins: the GAL4 DNA-binding domain fused to CDK4, GAL4db-CDK4; and the GAL4 activation domain fused to the proteins encoded by HeLa cDNAs, GAL4ad-cDNA. YPB2 was used as the recipient yeast as it is a strain that contains two chromosomal genes under the control of two different GAL4-dependent promoters: HIS3 and LacZ. YPB2 was transformed with a mixture of two plasmids encoding, respectively, the GAL4db-CDK4 and the GAL4ad-cDNA fusions; several clones were obtained that grew in the absence of histidine and that turned blue in the presence of β-gal. From DNA sequencing data it was determined that each of the positive clones derived from the same gene, although one group represented mRNAs with a shorter 3' end. The sequence of these cDNAs contained, in-phase with the GAL4ad, an open reading frame encoding a protein of 148 amino acids with a predicted molecular weight of 15,845 daltons (see SEQ ID Nos. 3 and 4). This protein is referred to hereinafter as INK4 (inhibitor of CDK4; see below). The sequence of p16INK4 was compared by standard methods with those present in the currently available data banks and no significant homologies were found.

To test if p16INK4 would specifically bind CDK4, YPB2 were cotransformed with the GAL4ad-p16INK4 fusion as well as with several target GAL4db fusion constructs containing, respectively, cdc2, CDK2, CDK4, CDK5, PCNA and Snfl (a fission yeast kinase). Transformed cells were plated with and without histidine. Only the GAL4db-CDK4 fusion interacted with GAL4ad-p16INK4 to an extent which allowed growth in the absence of histidine, indicating that this pair of fusion proteins specifically reconstituted a functional GAL4 activator able to enhance the expression of the HIS3 gene. The same result was obtained when the ability to transactivate the expression of the β-galactosidase gene was assayed.

The specificity of this interaction was further demonstrated in a cell-free system, by mixing in vitro translated ($^{35}$S)-labeled CDKs with a purified bacterially-produced fusion protein consisting of glutathione-S transferase (GST) linked to p16INK4 (17). The GST-p16INK4 fusion was recovered by binding to glutathione-sepharose beads and the association of each CDK was analyzed by gel electrophoresis. Consistent with the previous observations, GST-p16INK4 bound much more efficiently to CDK4 than to cdc2, CDK2 or CDK5.

Since the predicted molecular weight of p16INK4 is close to 16 Kd, the identity of p16INK4 as the CDK4-associated p16 protein found in transformed cell lines (see above) was determined. Two in vitro translation products of 15 KD and 17 KD were obtained from the p16INK4 cDNA. These products, as well as the CDK4-associated p16 protein from HeLa cells were treated with N-chlorosuccinimide. The partial NCS-proteolytic pattern of the 17 KD cDNAINK4-derived product was very similar to the pattern obtained with the CDK4-associated p16 protein from HeLa cells, strongly suggesting that the p16INK4 cDNA actually corresponds to p16. Partial digestion with V8 protease of the 17 KD cDNAINK4-derived product and p16 also yielded similar patterns. It is interesting to note that the p16INK4 protein overexpressed in insect cells has an electrophoretic mobility of 15 KD, and its NCS proteolytic map is identical to that obtained with the 15 KD cDNA derived product. This suggests that the actual p16INK4 found in human cells and the 17 KD in vitro translation product correspond to post-translationally modified proteins. The fact that the p16INK4 protein overexpressed in insect cells interacts with CDK4 suggests that this modification is not essential for the interaction (see below).

The identity between p16INK4 and the CDK4-associated protein p16 was further confirmed using antibodies raised against the purified GST-p16INK4 fusion protein. Several human cell lines were used for this experiment: a normal cell line WI38, derived from normal lung fibroblasts; the VA13 cell line derived from WI38 by transformation with the SV40 T-antigen; and HeLa cells. As set out above, anti-CDK4 immunoprecipitates of WI38 revealed the association of CDK4 with cyclin D1, PCNA, p21 and p16. In contrast, in VA13 and HeLa cells CDK4 is only associated with p16. Anti-p16INK4 immunoprecipitates contained a protein with an apparent molecular weight of 16 KD which was readily detectable in the two transformed cell lines, VA13 and HeLa but to a lesser extent in the normal cell line WI38. This protein not only had the same electrophoretic mobility as the p16 protein coimmunoprecipitated with anti-CDK4 serum, but also had an identical NCS partial proteolytic pattern. In addition to p16INK4 a protein of 33 Kd was observed in anti-p16 coimmunoprecipitates that was shown to be identical to CDK4 by V8-proteolytic mapping.

Northern analysis of the transcripts present in WI38 and VA13 cells indicated that the p16INK4 mRNA was around many times less abundant in WI38 cells compared to VA13 cells. This difference approximately corresponded to the observed difference in the amount of p16 protein between the two cell lines, suggesting the possibility that p16INK4 expression might be regulated at a transcriptional or post-transcriptional level. Indeed, in three non-virally transformed cell lines the expression of p16INK4 could not be detected even after overexposure of the gel.

To study the biochemical consequences of the interaction of p16INK4 with CDK4, active CDK4-cyclin D complexes have been reconstituted in vitro by standard protocols (Kato et al. *Genes Der* 7:331 (1993); and Ewen et al. *Cell* 73:487 (1993)). The three relevant components, CDK4, p16INK4 and cyclin D1, were expressed in baculovirus-infected insect cells. Extracts were prepared from metabolically ($^{35}$S)-labeled insect cells that separately overexpressed p16INK4, CDK4 or cyclin D1, as well as from cells overexpressing both CDK4 and cyclin D1. In response to increasing amounts of p16INK4, corresponding decreases in the ability of CDK4 to phosphorylate Rb was observed. This inhibition correlated with the association between p16INK4 and CDK4 as detected by immunoprecipitation. No inhibition was observed when CDK2-cyclin D2 complexes were used in a similar assay. To confirm that the inhibition of CDK4 was due to p16INK4, a His-tagged p16INK4 fusion protein (His-p16INK4) was created to have an amino terminal extension of 20 amino acids containing a tract of 6 histidine residues. This fusion protein was overexpressed in baculovirus-infected insect cells, and was purified by virtue of the high-affinity association of the histidine tract to nickel-agarose beads. The His-p16INK4 protein preparation was shown to be >90% pure, and inhibited the activity of the CDK4-cyclin D1complex under conditions similar to those used for inhibition by the whole lysates.

The role of the retinoblastoma gene product (Rb), appears to be as a cell cycle checkpoint which appears to at least act be sequestering transcription factors responsible for the proteins of S phase. In many carcinomas, p53 function is lost by mutation or deletion. Rb, on the other hand, is not apparently altered as often. However, because p16 down-regulates the CDK4/cyclin D complex, which acts to phosphorylate Rb, it is proposed herein that p16 loss in certain carcinomas can alleviate the effects of the Rb checkpoint and, in some manner of speaking, represent a checkpoint deficiency analogous to p53 loss. The loss of p16 would result in more effective phosphorylation of Rb and hence would remove the Rb-mediated inhibition of the cell cycle. Consistent with this notion, it is described below that in a variety of human tumor cells, such as cells which over-express a D-type cyclin, e.g. cyclin D1 or D2, the p16 gene is lost from the cell, e.g. homozygously deleted.

Moreover, as described in the examples below, the p16 gene was found to map to the human region 9p21–22, a known melanoma locus (Walker et al. (1994) *Oncogene* 9:819; Coleman et al. (1994) *Cancer Res* 54:344;Cheng et al. (1993) *Cancer Res* 53:4761; and Cannon-Albright et al. (1992) *Science* 258:1148). The chromosomal mapping was further confirmed by analysis of somatic cell hybrids through PCR amplification (using primers ex1A and ex13 of FIG. 2A). Somatic hybrids containing human chromosome 9 resulted in positive PCR products being applified.

Utilizing primers generated from the CDNA sequence of human p16 (SEQ ID No. 1) which are shown in FIG. 1, the genomic p16 gene was partially sequenced to determine intron/exon boundaries. The approximate sequences of the nucleic acid flanking Exon 1 and Exon 2 (see FIG. 1) are shown in FIGS. 2A and 2B and 3A–D respectively.

Genomic DNA was isolated from a variety of human tumor lines (Sambrook et al. *Molecular Cloning: A Laboratory Manual*, CSHL Press, Cold Spring Harbor, N.Y. (1989)) and was probed by PCR reactions for the presence or absence of p16 sequences. In particular, primers ex1A and ex13 (FIG. 2A) were used to score for exon 1 of p16, and primers ex14 and ex15 were likewise used to detect exon 2 of p16. As shown in FIG. 4, the p16 gene is disrupted in several tumor cell lines, confirming that p16 is indeed likely to be critical in cell transformation in certain cancerous cells. Moreover, probing of these cell lines with full length p16 cDNA (SEQ ID No. 1) demonstrated that in at least 3 of those cells apparently missing a portion of the p16 gene, the entire gene was in fact absent.

Based on immunoprecipitation experiments with anti-p16 antibodies, as well as oligonucleotide hybridization assays, it became apparent that the p16 protein represented by SEQ ID No. 2 is merely one member of a larger family of related cell cycle regulatory proteins. For instance, even under high stringency conditions, Southern hybridation experiments of mRNA from different tissue types has indicated that approximately 4 closely related transcripts are produced. These p16 homologs, members of the CCR-protein family, may have arisen by gene duplication (e.g. each CCR protein arises from a distinct gene) or from alternate exon splicing at the mRNA level, or a combination thereof.

Utilizing a probe consisting of the coding region of the human p16 gene, we have screened a mouse embryonal stem cell library and have isolated a genomic clone containing the coding region for a mouse homolog of the human p16 gene described above. This clone was isolated under low to moderate stringency conditions (1×SSC at 50° C.). This DNA (14 kB) has been cloned in two independent pieces and the restriction map for nine restriction endonucleases has been performed (see FIG. 5). The mouse CCR gene has been completely sequenced and the coding region is apparently made up of only two exons that have been located in the restriction map by Southern hybridization. The apparent molecular weight of the mouse CCR protein is 13.5 kDa, and the nucleic acid and amino acid sequence of the mouse p16 homolog, termed herein "p13.5", is given in SEQ ID No. 3 and 4 respectively.

Moreover, utilizing degenerate probes based on the most highly conserved sequences between the human p16 clone and mouse p13.5 clone (e.g. between residues Met-52 through Gly-135 of human p16 and Met-1 through Gly-83 of mouse p13.5), we have isolated a number of human p16 homologs.

The present invention will now be illustrated by the following examples, which are not intended to be limiting in any way.

EXAMPLE 1

Demonstration of Selective Subunit Rearrangement of Cell Cycle Complexes In Association With Cellular Transformation by a DNA Tumor Virus or Its Oncogenic Product (i) Cellular Transformation With DNA Tumor Virus SV40 Is Associated With Subunits Rearrangement of Cell Cycle Complexes Preparation of [$^{35}$S] methionine-labelled cell lysates and polyacrylamide gel electrophoresis were as described above, as well as described in PCT Publication No. WO92/20796. Cell lysates were prepared from either human normal diploid fibroblast cells WI38 or DNA tumor virus SV40 transformed WI38 cells, VA13. Cell lysates were immunoprecipitated with antibodies against each cell cycle gene products.

(ii) Subunit Rearrangements of Cell Cycle Complexes In Two Different Pair Cell Lines Methods for preparation of cell lysates are the same as described above. Two different pair cell lines were used in these experiments. HSF43 is a normal human diploid fibroblast cell line and CT10 (full name CT10-2C-T1) is a derivative of HSF43 transformed by SV40 large tumor antigen. CV-1 is an African green monkey kidney cell line and COS-1 is a derivative of CV-1 transformed by SV40.

(iii) Cellular Transformation by DNA Tumor Virus SV40 Is Associated With Rearrangement of PCNA Subunit of Cell Cycle Complexes Preparation of cell lysate, electrophoresis, and Western blotting conditions are the same as described above. Normal human diploid fibroblast cell lines and their SV40 transformed cell lines are described above. Immunoprecipitates derived from each antibody were separated on polyacrylamide gels and blotted with anti-PCNA antibody.

(iv) Cellular Transformation by DNA Tumor Virus SV40 Is Associated With Rearrangement of CDK4 Subunit of Cell Cycle Complexes Preparation of cell lysate, electrophoresis, and Western blotting conditions are the same as previously described. Normal human diploid fibroblast cell lines and their SV40 transformed cell lines are described above. Immunoprecipitates derived from each antibody were separated on polyacrylamide gels and blotted with anti-CDK4 antibody.

EXAMPLE 2

Cloning of p16$^{INK4}$, an inhibitor of CDK4 activity (i) Cloning of p16$^{INK4}$ using the two hybrid assay Saccharomyces cerevisiae YPB2 cells were transformed simultaneously with a plasmid containing a GAL4db-p16INK4 fusion and with a plasmid containing, respectively, the GAL4ad fused to cdc2 (CDK1), CDK2, CDK4, CDK5, PCNA (proliferating cell nuclear antigen), and the fission yeast kinase Snf 1. After growing cells in medium selective for both plasmids (minus tryptophan and minus leucine), two colonies were picked randomly and were streaked in plates that either contained or lacked histidine. The ability to grow in the absence of histidine depends on the expression of the HIS3 gene that is under a GAL4-responsive promoter and, therefore, indicates that a functional GAL4 activator has been reconstituted through the interaction of p16INK4 with the corresponding target protein.

(ii) Interaction of p16$^{INK4}$ CDKs

Purified bacterially-produced GSTp16INK4 fusion protein was mixed with ($^{35}$S)-labeled in vitro translated cdc2, CDK2, CDK4 and CDK5. Mixtures contained 0.5 μg of purified GST-p16INK4 and an equivalent amount of in vitro translated protein (between 0.5 to 5 μl; TNT Promega) in a final volume of 200 μl of a buffer containing 50 mM Tris-HCl pH 8, 120 mM NaCl and 0.5% Nonidet P-40. After 1 h at 4° C., 15 μl of glutathione-agarose beads were added and incubation was resumed for an additional hour. Beads were recovered by centrifugation, washed 4 times with the incubation buffer, and mixed with standard protein-gel loading buffer. Samples were loaded into a 15% polyacryllamide gel and ($^{35}$S)-labeled proteins were detected by fluorography. The GSTp16INK4 fusion protein was overexpressed in the pGEX-KG vector and purified by standard techniques. The in vitro translation templates were derived from the pBluescript vector (Stratagene).

(iii) Proteolytic mapping of p16$^{INK4}$

The in vitro translated ($^{35}$S)-labeled p16INK4 (TNT Promega) was obtained using the p16INK4 cDNA cloned into pBluescript vector (Stratagene) as a template, and the CDK4-associated p16 protein was co-immunoprecipitated with an anti-CDK4 serum from metabolically ($^{35}$S)-labeled HeLa cells lysates Partial proteolysis was done over the corresponding gel slices after extensive equilibration in a buffer and digestion was accomplished by addition of NCS at different concentrations. The products were run in a 17.5% polyacrylamide gel and detected in a phosphoimager Fujix 2000.

(iv) Detecting the effects of p16$^{INK4}$ on CDK4-cyclin D complexes

Baculovirus-infected insect cells overexpressing p16INK4, CDK4, cyclin D1, or both CDK4 and cyclin D1together were metabolically ($^{35}$S)-labeled. The different incubation mixtures were composed by extracts containing p16INK4, CDK4, cyclin D1 and both CDK4 and cyclin D1, and were immunoprecipitated with anti-p16INK4, serum, anti-CDK4 serum without any previous preincubation, and anti-CDK serum preincubated with the peptide originally used to raise the antiserum and anti-cyclin D1 serum. Immunoprecipitates were then analyzed by SDS-PAGE.

EXAMPLE 3

Chromosomal Mapping of p16$^{INK4}$

Genomic clones of the human p16 gene were isolated by stringency screening (68° C. with 0.1×SSC wash) of a λFIXII human genomic library (Strategene) with cDNA probes. Isolated phage clones were confirmed by high stringency Southern hybridization and/or partial sequence analysis. Purified whole phage DNA was labelled for fluorescent in situ hybridization (FISH) analysis.

FISH analysis was performed using established methods (Demetrick et al. (1994) *Cytogenet Cell Genet* 66:72–74; Demetrick et al. (1993) *Genomics* 18: 144–147; and DeMarini et al. (1991) *Environ Mol Mutagen* 18:222–223) on methotrexate or thymidine synchronized, phytohemagglutinin stimulated, normal peripheral blood lymphocytes. Suppression with a mixture of sonicated human DNA and cot1 DNA was required to reduce the background. The stained slides were counterstained with propidiem iodide (for an R banding pattern) or DAPI and actinomycin D (for a DA-DAPI banding pattern), mounted in antifade medium and visualized utilizing a Zeiss Axiphot microscope. Between 30 and 100 mitotises were examined for each gene location. Photographs were taken using a cooled CCD camera. Alignment of three color fluorescence was done under direct visualization through a triple bandpass filter (FITC/Texas Red/DAPI). The p16 gene was visualized to map to 9p21–22.

EXAMPLE 4

Cloning Of Mouse p16 Homolog

Utilizing a probe consisting of the coding region of the human p16 gene, we have screened a mouse embryonal stem cell library and have isolated a genomic clone containing the coding region for a mouse homolog of the human p16 gene described above. This clone was isolated under low to moderate stringency conditions (1×SSC at 50° C.). This DNA (14 kB) has been cloned in two independent pieces and the restriction map for nine restriction endonucleases has been performed (see FIG. 5). The mouse CCR gene has been completely sequenced and the coding region is apparently made up of only two exons that have been located in the restriction map by Southern hybridization. The apparent molecular weight of the mouse CCR protein is 13.5 kDa, and the nucleic acid and amino acid sequence of the mouse p16 homolog, termed herein "p13.5", is given in SEQ ID No. 3 and 4 respectively.

EXAMPLE 5

Generating a Transgenic Mouse p13.5 Knockout

The disruptive construct is formed by the two DNA regions of approx. 3–4 Kb flanking the p13.5 gene. These DNA pieces are cloned at both sides of a gene marker that will be used to select the mouse embryonal stem (ES) cells that have incorporated this DNA after transfection. Regions which are homologous to the p16 locus are in turn flanked by another marker which allows selection against cells which have incorporated the disruption vector by non-homologous recombination (e.g. at a locus other than that of the mouse p13.5 gene). Those cells where insertion has occurred in the appropriate position are injected into mouse blastocytes and implanted into the appropriate female mice following standard protocols (*Manipulating the Mouse Embryo*, (Cold Spring Harbor Laboratory Press, Cold Spring Harbor, N.Y., 1986; and Jaenisch (1988) *Science* 240:1468–1474.)

Chimeric pups resulting from the engineered blastocysts can be identified by a coat color marker specific to the transfected ES cells (agouti). Mice with high degrees of chimerism are crossed to identify those with chimeric germ lines and to generate non-chimeric heterozygous disruptants. Homozygous disruptants are derived by breeding the non-chimeric heterozygotes.

All of the above-cited references and publications are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

---

We claim:

1. A substantially pure nucleic acid having a nucleotide sequence which encodes a p16 polypeptide, wherein said nucleic acid hybridizes under stringent condition to a nucleic acid of SEQ ID NO: 1, and wherein said p16 polypeptide binds a cyclin dependent kinase (CDK).

2. The nucleic acid of claim 1, wherein said CDK is selected from the group consisting of CDK4 and CDK 6.

3. The nucleic acid of claim 1, wherein said p16 polypeptide encoded by said nucleic acid functions in one of either role of an agonist of cell cycle regulation or an antagonist of cell cycle regulation.

4. The nucleic acid of claim 1, wherein the portion of said nucleic acid which encodes the p16 polypeptide hybridizes under stringent conditions to a nucleic acid probe corresponding to at least 12 consecutive nucleotides of a nucleic acid sequence of SEQ ID No: 1.

5. The nucleic acid of claim 1, further comprising a transcriptional regulatory sequence operably linked to said nucleotide sequence so as to render said nucleotide sequence suitable for use as an expression vector.

6. An expression vector, capable of replicating in at least one of a prokaryotic cell and eukaryotic cell, comprising the nucleic acid of claim 5.

7. The nucleic acid of claim 2, wherein said CDK is CDK4.

8. A recombinant gene comprising a nucleotide sequence which encodes a p16 polypeptide, having an amino acid sequence of SEQ ID No: 2 capable of binding to a cyclin dependent kinase (CDK), which nucleotide sequence is operably linked to a transcriptional regulatory sequence in an open reading frame.

9. The nucleic acid of claim 8, wherein said CDK is CDK4.

10. A substantially purified nucleic acid encoding a polypeptide which binds to a cyclin dependent kinase, and wherein said nucleic acid has a nucleotide sequence which hybridizes under stringent conditions to at least 25 consecutive nucleotides of sense or antisense sequence of SEQ ID No: 1, or naturally occurring mutants thereof.

11. The nucleic acid of claim 10, which nucleotide sequence hybridizes under stringent conditions to at least 50 consecutive nucleotides of sense or antisense sequence of SEQ ID No: 1.

12. The nucleic acid of claim 10, which nucleic acid further comprises a label group attached thereto and able to be detected.

13. The nucleic acid of claim 1, which nucleic acid encodes a p16 polypeptide having an amino acid sequence designated in SEQ ID No. 2.

14. An isolated nucleic acid encoding a human p16 polypeptide.

15. A recombinant gene comprising a nucleotide sequence which hybridizes under stringent conditions to the nucleotide sequence of SEQ ID No: 1, said nucleotide sequence operably linked to a transcriptional regulatory sequence in an open reading frame and translatable to a polypeptide capable of binding to a cyclin dependent kinase (CDK).

16. The recombinant gene of claim 15, which is derived from a cDNA clone.

17. The recombinant gene of claim 15, which is derived from a genomic clone and includes intronic nucleotide sequences disrupting said nucleotide sequence of a nucleic acid sequence of SEQ ID No: 1.

18. The recombinant gene of claim 15, wherein said polypeptide is a fusion protein.

19. The recombinant gene of claim 18, wherein said fusion protein is functional in a two-hybrid assay.

20. The recombinant gene of claim 15, which polypeptide specifically binds a cyclin dependent kinase (CDK) selected from the group consisting of CDK4 and CDK6.

21. The recombinant gene of claim 20, wherein said CDK is CDK4.

22. A substantially purified nucleic acid having a nucleotide sequence which hybridizes under stringent conditions to at least 25 consecutive nucleotides of sense or antisense sequence of SEQ ID No: 1, or naturally occurring mutants thereof.

23. The nucleic acid of claim 22, which nucleotide sequence hybridizes under stringent conditions to at least 50 consecutive nucleotides of sense or antisense sequence of SEQ ID No: 1.

24. A nucleic acid which hybridizes under stringent conditions to the nucleotide sequence designated by SEQ ID No: 1 and specifically detects a human p16 gene or mRNA.

25. The nucleic acid of claim 15, wherein said polypeptide is a fusion protein.

26. The nucleic acid of any one of claims 1, 2, 4, and 7, wherein the encoded polypeptide inhibits a kinase activity associated with cdk.

27. The recombinant gene of any one of claims 15, 20, and 21, wherein the encoded polypeptide inhibits a kinase activity associated with cdk.

28. The nucleic acid of claim 5, wherein said transcriptional regulatory sequence is heterologous with respect to the nucleic acid sequence.

29. The recombinant gene of claim 15, wherein said transcriptional regulatory sequence is heterologous with respect to the nucleic acid sequence.

* * * * *

UNITED STATES PATENT AND TRADEMARK OFFICE
CERTIFICATE OF CORRECTION

PATENT NO. : 5,889,169
DATED : March 30,1999
INVENTOR(S) : David H. Beach, ET AL.

It is certified that error appears in the above-identified patent and that said Letters Patent is hereby corrected as shown below:

On the title page, item[75] " Delete the following inventors:

" Douglas J. Demetrick, E.Northport;"

" Dawn E. Quelle, Cordova, Tenn; " and

" Charles J. Sherr, Memphis Tenn; "

Signed and Sealed this

Twenty-fifth Day of May, 1999

*Attest:*

Q. TODD DICKINSON

*Attesting Officer*     *Acting Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 994 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 41..508

( x i ) SEQUENCE DESCRIPTION: SEQ ID NO:1:

```
CGGAGAGGGG GAGAACAGAC AACGGGCGGC GGGGAGCAGC ATG GAT CCG GCG GCG         55
                                            Met Asp Pro Ala Ala
                                              1               5

GGG AGC AGC ATG GAG CCT TCG GCT GAC TGG CTG GCC ACG GCC GCG GCC        103
Gly Ser Ser Met Glu Pro Ser Ala Asp Trp Leu Ala Thr Ala Ala Ala
              10              15                      20

CGG GGT CGG GTA GAG GAG GTG CGG GCG CTG CTG GAG GCG GTG GCG CTG        151
Arg Gly Arg Val Glu Glu Val Arg Ala Leu Leu Glu Ala Val Ala Leu
             25              30                      35

CCC AAC GCA CCG AAT AGT TAC GGT CGG AGG CCG ATC CAG GTC ATG ATG        199
Pro Asn Ala Pro Asn Ser Tyr Gly Arg Arg Pro Ile Gln Val Met Met
            40              45                  50

ATG GGC AGC GCC CGA GTG GCG GAG CTG CTG CTG CTC CAC GGC GCG GAG        247
Met Gly Ser Ala Arg Val Ala Glu Leu Leu Leu Leu His Gly Ala Glu
     55                      60                 65

CCC AAC TGC GCC GAC CCC GCC ACT CTC ACC CGA CCC GTG CAC GAC GCT        295
Pro Asn Cys Ala Asp Pro Ala Thr Leu Thr Arg Pro Val His Asp Ala
 70                 75                  80                      85

GCC CGG GAG GGC TTC CTG GAC ACG CTG GTG GTG CTG CAC CGG GCC GGG        343
Ala Arg Glu Gly Phe Leu Asp Thr Leu Val Val Leu His Arg Ala Gly
                 90                 95                 100

GCG CGG CTG GAC GTG CGC GAT GCC TGG GGC CGT CTG CCC GTG GAC CTG        391
Ala Arg Leu Asp Val Arg Asp Ala Trp Gly Arg Leu Pro Val Asp Leu
            105                 110                115

GCT GAG GAG CTG GGC CAT CGC GAT GTC GCA CGG TAC CTG CGC GCG GCT        439
Ala Glu Glu Leu Gly His Arg Asp Val Ala Arg Tyr Leu Arg Ala Ala
            120             125                 130

GCG GGG GGC ACC AGA GGC AGT AAC CAT GCC CGC ATA GAT GCC GCG GAA        487
Ala Gly Gly Thr Arg Gly Ser Asn His Ala Arg Ile Asp Ala Ala Glu
    135                 140                 145
```

```
GGT CCC TCA GAC ATC CCC GAT TGAAAGAACC AGAGAGGCTC TGAGAAACCT        538
Gly Pro Ser Asp Ile Pro Asp
150                 155

CGGGAAACTT AGATCATCAG TCACCGAAGG TCCTACAGGG CCACAACTGC CCCCGCCACA   598

ACCCACCCCG CTTTCGTAGT TTTCATTTAG AAAATAGAGC TTTTAAAAAT GTCCTGCCTT   658

TTAACGTAGA TATAAGCCTT CCCCCACTAC CGTAAATGTC CATTTATATC ATTTTTTATA   718

TATTCTTATA AAAATGTAAA AAAGAAAAAC ACCGCTTCTG CCTTTTCACT GTGTTGGAGT   778

TTTCTGGAGT GAGCACTCAC GCCCTAAGCG CACATTCATG TGGGCATTTC TTGCGAGCCT   838

CGCAGCCTCC GGAAGCTGTC GACTTCATGA CAAGCATTTT GTGAACTAGG GAAGCTCAGG   898

GGGGTTACTG GCTTCTCTTG AGTCACACTG CTAGCAAATG GCAGAACCAA AGCTCAAATA   958

AAAATAAAAT TATTTTCATT CATTCACTCA AAAAAA                            994
```

( 2 ) INFORMATION FOR SEQ ID NO:2:

( i ) SEQUENCE CHARACTERISTICS:
        ( A ) LENGTH: 156 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asp Pro Ala Ala Gly Ser Ser Met Glu Pro Ser Ala Asp Trp Leu
 1               5                  10                  15

Ala Thr Ala Ala Ala Arg Gly Arg Val Glu Val Arg Ala Leu Leu
            20                  25                  30

Glu Ala Val Ala Leu Pro Asn Ala Pro Asn Ser Tyr Gly Arg Arg Pro
            35                  40                  45

Ile Gln Val Met Met Met Gly Ser Ala Arg Val Ala Glu Leu Leu Leu
        50                  55                  60

Leu His Gly Ala Glu Pro Asn Cys Ala Asp Pro Ala Thr Leu Thr Arg
65                  70                  75                  80

Pro Val His Asp Ala Ala Arg Glu Gly Phe Leu Asp Thr Leu Val Val
                85                  90                  95

Leu His Arg Ala Gly Ala Arg Leu Asp Val Arg Asp Ala Trp Gly Arg
                100                 105                 110

Leu Pro Val Asp Leu Ala Glu Glu Leu Gly His Arg Asp Val Ala Arg
            115                 120                 125

Tyr Leu Arg Ala Ala Ala Gly Gly Thr Arg Gly Ser Asn His Ala Arg
            130                 135                 140

Ile Asp Ala Ala Glu Gly Pro Ser Asp Ile Pro Asp
145                 150                 155
```

( 2 ) INFORMATION FOR SEQ ID NO:3:

( i ) SEQUENCE CHARACTERISTICS:
        ( A ) LENGTH: 853 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 213..587

( x i ) SEQUENCE DESCRIPTION: SEQ ID NO:3:

```
GGAGTACAGC AGCGGGAGCA TGGGTCGCAG GTTCTTGGTC ACTGTAAGGA TTCAGCGCGC    60
```

```
GGGCCGCCCA CTCCAAGAGA GGGTTTTCTT GGTGAAGTTC GTGCGATCCC GGAGACCCAG         120

GACAGCGAGC TGCGCTCTGG CTTTCGTGAA CATGTTGTTG AGGCTAGAGA GGATCTTGAG         180

AAGAGGGCCG CACCGGAATC CTGGACCAGG TG ATG ATG ATG GGC AAC GTT CAC          233
                                   Met Met Met Gly Asn Val His
                                    1               5

GTA GCA GCT CTT CTG CTC AAC TAC GGT GCA GAT TCG AAC TGC GAG GAC           281
Val Ala Ala Leu Leu Leu Asn Tyr Gly Ala Asp Ser Asn Cys Glu Asp
         10                  15                  20

CCC ACT ACC TTC TCC CGC CCG GTG CAC GAC GCA GCG CGG GAA GGC TTC           329
Pro Thr Thr Phe Ser Arg Pro Val His Asp Ala Ala Arg Glu Gly Phe
     25                  30                  35

CTG GAC ACG CTG GTG GTG CTG CAC GGG TCA GGG GCT CGG CTG GAT GTG           377
Leu Asp Thr Leu Val Val Leu His Gly Ser Gly Ala Arg Leu Asp Val
40                   45                  50                  55

CGC GAT GCC TGG GGT CGC CTG CCG CTC GAC TTG GCC CAA GAG CGG GGA           425
Arg Asp Ala Trp Gly Arg Leu Pro Leu Asp Leu Ala Gln Glu Arg Gly
                 60                  65                  70

CAT CAA GAC ATC GTG CGA TAT TTG CGT TCC GCT GGG TGC TCT TTG TGT           473
His Gln Asp Ile Val Arg Tyr Leu Arg Ser Ala Gly Cys Ser Leu Cys
             75                  80                  85

TCC GCT GGG TGG TCT TTG TGT ACC GCT GGG AAC GTC GCC CAG ACC GAC           521
Ser Ala Gly Trp Ser Leu Cys Thr Ala Gly Asn Val Ala Gln Thr Asp
         90                  95                 100

GGG CAT AGC TTC AGC TCA AGC ACG CCC AGG GCC CTG GAA CTT CGC GGC           569
Gly His Ser Phe Ser Ser Ser Thr Pro Arg Ala Leu Glu Leu Arg Gly
    105                 110                 115

CAA TCC CAA GAG CAG AGC TAAATCCGCC TCAGCCCGCC TTTTCTTCT                   617
Gln Ser Gln Glu Gln Ser
120                 125

TAGCTTCACT TCTAGCGATG CTAGCGTGTC TAGCATGTGG CTTTAAAAAA TACATAATAA         677

TGCTTTTTTT GCAATCACGG GAGGGAGCAG AGGGAGGGAG CAGAAGGAGG GAGGGAGGGA         737

GGGAGGGACC TGGACAGGAA AGGAATGGCA TGAGAAACTG AGCGAAGGCG GCCGCGAAGG         797

GAATAATGGC TGGATTGTTT AAAAAAATAA AATAAAGATA CTTTTTAAAA TGTCAA            853
```

(2) INFORMATION FOR SEQ ID NO:4:

(i) SEQUENCE CHARACTERISTICS:
        (A) LENGTH: 125 amino acids
        (B) TYPE: amino acid
        (D) TOPOLOGY: linear (ii) MOLECULE TYPE: protein (xi) SEQUENCE DESCRIPTION: SEQ ID NO:4:

```
Met Met Met Gly Asn Val His Val Ala Ala Leu Leu Leu Asn Tyr Gly
 1               5                  10                  15

Ala Asp Ser Asn Cys Glu Asp Pro Thr Thr Phe Ser Arg Pro Val His
             20                  25                  30

Asp Ala Ala Arg Glu Gly Phe Leu Asp Thr Leu Val Val Leu His Gly
             35                  40                  45

Ser Gly Ala Arg Leu Asp Val Arg Asp Ala Trp Gly Arg Leu Pro Leu
     50                  55                  60

Asp Leu Ala Gln Glu Arg Gly His Gln Asp Ile Val Arg Tyr Leu Arg
65                   70                  75                  80

Ser Ala Gly Cys Ser Leu Cys Ser Ala Gly Trp Ser Leu Cys Thr Ala
                 85                  90                  95

Gly Asn Val Ala Gln Thr Asp Gly His Ser Phe Ser Ser Ser Thr Pro
```

|  | 100 |  |  |  |  | 105 |  |  |  |  | 110 |
|---|---|---|---|---|---|---|---|---|---|---|---|
| Arg | Ala | Leu | Glu | Leu | Arg | Gly | Gln | Ser | Gln | Glu | Gln | Ser |
|  |  | 115 |  |  |  | 120 |  |  |  |  | 125 |